United States Patent
Michener et al.

(10) Patent No.: US 12,362,039 B2
(45) Date of Patent: Jul. 15, 2025

(54) BACTERIAL QUANTITATIVE TRAIT-LOCUS MAPPING

(71) Applicant: UT-Battelle, LLC, Oak Ridge, TN (US)

(72) Inventors: Joshua K. Michener, Oak Ridge, TN (US); Daniel A. Jacobson, Oak Ridge, TN (US); Delyana Vasileva, Knoxville, TN (US); Jared Streich, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1280 days.

(21) Appl. No.: 16/901,514

(22) Filed: Jun. 15, 2020

(65) Prior Publication Data

US 2020/0395096 A1 Dec. 17, 2020

Related U.S. Application Data

(60) Provisional application No. 62/861,378, filed on Jun. 14, 2019.

(51) Int. Cl.
| | |
|---|---|
| *G16B 20/40* | (2019.01) |
| *C12N 15/03* | (2006.01) |
| *C12N 15/90* | (2006.01) |
| *C12Q 1/02* | (2006.01) |
| *G16B 20/00* | (2019.01) |
| *G16B 25/00* | (2019.01) |

(52) U.S. Cl.
CPC ............. *G16B 20/40* (2019.02); *C12N 15/03* (2013.01); *C12N 15/902* (2013.01); *C12Q 1/02* (2013.01); *G16B 25/00* (2019.02); *G16B 20/00* (2019.02)

(58) Field of Classification Search
CPC ........ C12N 15/03; C12N 15/902; C12Q 1/02; G16B 20/00
See application file for complete search history.

(56) References Cited

PUBLICATIONS

EQTL Analysis. Methods in Molecular Biology. vol. 2082, Humana, New York NY. Online Dec. 18, 2019. (Year: 2019).*
Vasileva et al. Bacterial quantitative trait-loci (QTL) mapping—a novel method for identification of genetic determinants affecting establishment of allopatric bacteria. Jan. 2020. 2 pages. https://genomicsscience.energy.gov/wp-content/uploads/2022/01/Abraham_Vasileva_Revised-20220125-200351.pdf (Year: 2020).*
Bauby et al. Microbiology (2003), 149, 689-693 (Year: 2003).*
Dai et al. Metab Eng. Jan. 2005;7(1):45-52 (Year: 2005).*
Gong et al. Biotechnology Advances 27 (2009) 996-1005 (Year: 2009).*
Hegazy & Moharam. Journal of Genetic Engineering and Biotechnology, 2010, 8(2): 67-74 (Year: 2010).*
Miles, C. & Wayne, M. (2008) Quantitative trait locus (QTL) analysis. NatureEducation 1(1):208 (Year: 2008).*
Hopwood. Ann. Rev. Microbial. 1981. 35:237-72 (Year: 1981).*
Geneious 11.1 User Manual, published Jul. 16, 2018 by Biomatters Ltd (Year: 2018).*
Calus and Vandenplas Genet Sel Evol (2018) 50:34 (Year: 2018).*
Weighill et al. Front. Genet., May 30, 2019 Sec. Computational Genomics vol. 10—2019 (Year: 2019).*
Zojer et al. PeerJ. 2017; 5: e2997 (Year: 2017).*
Biot-Pelletier, D. et al., "Evolutionary engineering by genome shuffling", Appl. Microbiol. Biotechnol., 98: 3877-3887 (2014).
Cowley, L.A. et al., "Evolution via recombination: Cell-to-cell contact facilitates larger recombination events in *Streptococcus pneumoniae*", PLOS Genet., 14, pp. 1-23, e1007410 (2018).
Croucher, N.J. et al., "A High-Resolution View of Genome-Wide Pneumococcal Transformation", PLOS Pathog., vol. 8, No. 6, pp. 1-15, e1002745 (2012).
Derbyshire, K.M. et al., "Distributive Conjugal Transfer: New Insights into Horizontal Gene Transfer and Genetic Exchange in Mycobacteria" ; Microbiol Spectr, 2, pp. 1-19 (2014).
Didelot, X. et al., "Impact of recombination on bacterial evolution", Trends Microbiol., 18(7): 315-322 (2010).
Dordet-Frisoni, E. et al., "Chromosomal Transfers in Mycoplasmas: When Minimal Genomes Go Mobile", MBio, 5(6): 1-11, e01958 (2014).
Dordet-Frisoni, E. et al., " Mycoplasma Chromosomal Transfer: A Distributive, Conjugative Process Creating an Infinite Variety of Mosaic Genomes", Front. Microbiol., 10, 2441, pp. 1-16 (2019).
Ega, S.L. et al., "Comparative Analysis of Structural Variations Due to Genome Shuffling of Bacillus Subtilis VS15 for Improved Cellulase Production", International J. of Mol. Sci., 21, 1299, pp. 1-21 (2020).
Gray, T.A. et al., "Distributive Conjugal Transfer in Mycobacteria Generates Progeny with Meiotic-Like Genome-Wide Mosaicism, Allowing Mapping of a Mating Identity Locus" , PLOS Biol., 11, e1001602 (2013).
Gray, T.A. et al., "Blending genomes: distributive conjugal transfer in mycobacteria, a sexier form of HGT", Mol. Microbiol., 108(6): 601-613 (2018).
Hopwood, D.A. et al., "Genetic recombination protoplast fusion Streptomyces", Nature, 268, pp. 171-174 (1977).

(Continued)

*Primary Examiner* — Richard A Schnizer
*Assistant Examiner* — Amanda M Zahorik
(74) *Attorney, Agent, or Firm* — Scully, Scott, Murphy & Presser, P.C.

(57) ABSTRACT

This disclosure provides methods for performing quantitative-trait loci (QTL) analysis in bacteria. The methods of the instant disclosure utilize multiple rounds of protoplast fusion-induced genomic recombination to break genetic linkages in bacterial genomes. The methods of the instant disclosure allow determining which genetic elements (QTL) are associated with phenotypic al features.

21 Claims, 17 Drawing Sheets

Specification includes a Sequence Listing.

(56) References Cited

PUBLICATIONS

Luna-Flores, C.H. et al., "Improved production of propionic acid using genome shuffling", Biotechnology Journal, 12.2:1600120, pp. 1-14 (2017).

Magocha, T.A. et al., "Improvement of industrially important microbial strains by genome shuffling: Current status and future prospects", Bioresour. Technol., 257, pp. 281-289 (2018).

Mell, J.C. et al., "Extensive Cotransformation of Natural Variation into Chromosomes of Naturally Competent Haemophilus influenzae", G3 (Bethesda), 4, pp. 717-731 (2014).

Mortimer, T.D. et al., "Genomic Signatures of Distributive Conjugal Transfer among Mycobacteria ", Genome Biol. Evol., 6(9): 2489-2500 (2014).

Patnaik, R. et al., "Genome shuffling of Lactobacillus for improved acid tolerance", Nat. Biotechnol., 20, pp. 707-712 (2002).

Petri, R. et al., "Dealing with complexity: evolutionary engineering and genome shuffling", Curr. Opin. Biotechnol., 15, pp. 298-304 (2004).

Schaeffer, P. et al., " Fusion of bacterial Protoplasts", PNAS, 73(6): 2151-2155 (1976).

She, R. et al., "Mapping Causal Variants with Single-Nucleotide Resolution Reveals Biochemical Drivers of Phenotypic Change", Cell, 172, pp. 478-490 (2018).

Wang, W. et al., "Genome shuffling enhances stress tolerance of Zymomonas mobilis to two inhibitors", Biotechnol. Biofuels, 12:288, pp. 1-12 (2019).

Zhang, Y.X., et al., "Genome shuffling leads to rapid phenotypic improvement in bacteria", Nature, 415, pp. 644-646 (2002).

Wang, W., et al., "Genome shuffling enhances stress tolerance of Zymomonas mobilis to two inhibitors", Biotechnol Biofuels, Received Mar. 12, 2019, Accepted Dec. 5, 2019, Published online Dec. 16, 2019, pp. 1-12, 12:288.

* cited by examiner

SHUFFLE PARENTAL BACTERIA

STRAIN A1          STRAIN B1

SEQUENCE LIBRARY OF ISOLATE GENOMES

BACTERIAL QUANTITATIVE TRAIT-LOCUS MAPPING

CROSS REFERENCE TO RELATED APPLICATION

This application claims the benefit of priority from U.S. Provisional Application No. 62/861,378, filed Jun. 14, 2019, the entire contents of which are incorporated herein by reference.

STATEMENT REGARDING FEDERALLY SPONSORED RESEARCH OR DEVELOPMENT

This disclosure was made with government support under a research project supported by Prime Contract No. DE-AC05-00OR22725 awarded by the U.S. Department of Energy. The government has certain rights in this invention.

INCORPORATION BY REFERENCE OF SEQUENCE LISTING

The Sequence Listing in the ASCII text file, named as 38310_3930_1_SequenceListing.txt of 1 KB, created on Jun. 9, 2020, and submitted to the United States Patent and Trademark Office via EFS-Web, is incorporated herein by reference.

BACKGROUND

Many organisms recombine their own DNA with other compatible individuals such that sub-components of each parent's genome are shuffled in the next generation. This new generation receives novel combinations of genes and alleles from both parents that can be used to overcome environment selection pressures. Sexual recombination is normal in eukaryotes and, through human selection, agriculturally relevant traits have been bred into wild species, examples include cattle from bison or cereals from grasses. In modern breeding, quantitative trait loci mapping and genomic selection play a large part of creating better breeding lines for agricultural species. Bacteria do not natively perform sexual recombination at the same scale as eukaryotes, though mechanisms are known that provide other routes for genomic recombination.

Homologous recombination in the form of uptake and integration of DNA from exogenous sources has played a profound role in shaping microbial evolution and speciation. However, genetic transfer and recombination are less common in natural bacterial populations and thus difficult to characterize in detail. While a number of computational methods have been developed to estimate the relative rates and distribution of recombination events based on genome sequences of extant bacteria, these analyses are confounded by historical selection on recombinant strains. Direct measurements of recombination parameters on a genome-wide scale are technically challenging because recombination patterns can be significantly affected by efficiencies and mechanistic specificities of DNA transfer. To date, most experimental estimates of recombination rates have been conducted by in vitro transformation of naturally competent bacteria, but under these conditions transfer is typically limited to only small regions of the genome. A greater portion of chromosomal DNA (~10-25%) spanning hundreds of genes can be exchanged between bacteria through some unconventional conjugal mechanisms resembling Hfr-based transfer in *Escherichia coli*. Mycobacterial distributive conjugal transfer and mycoplasma chromosomal transfer can promote simultaneous transfer of multiple large donor chromosomal fragments to the recipient cells creating chimeric transconjugant genomes with unique recombination landscapes. Although these studies have provided an invaluable insight into the genetics of recombination, they were also restricted in scale and scope due to computational limitations. Methods to routinely generate and analyze highly recombined bacterial strains from diverse clades are still lacking.

High frequencies of genetic transfer and recombination on a genome-wide scale in bacteria can be achieved by protoplast fusion. In this genetic engineering method, bacterial cells are stripped of their outer layer(s) and chemically fused together, allowing recombination between the parental chromosomes. Originally used for routine genetic manipulation, protoplast fusion has been widely adopted as a strategy to generate microorganisms with improved phenotypes for biotechnological applications by combining beneficial alleles from different strains and even species. For instance, combinatorial shuffling of complete genomes by recursive fusion of protoplast populations has been employed to engineer multigenic traits for which the underlying molecular mechanisms are poorly understood, such as tolerance to stress conditions and production of diverse metabolites. Multiple crossover events are generally assumed to occur across the entire genome during this process giving rise to mosaic chromosomes with unique phenotypic potential, analogous to meiotic recombination products in sexually reproducing organisms. However, surprisingly, the exact nature of the chromosomal rearrangements resulting from large-scale shuffling experiments has received little attention and to date there are few studies reporting detailed analyses of sequenced bacterial shuffled genomes. Furthermore, due to strong selective pressure for the desired phenotypes these analyses could not capture the full extent of recombination occurring between the parental chromosomes in protoplast fusants.

Quantitative Trait-Locus (QTL) mapping is an established technique in eukaryotic genetics that is used to identify genetic loci affecting a phenotype of interest. In this approach, two parental organisms are crossbred, potentially followed by inbreeding of the progeny. A panel of offspring is collected, genotyped, and phenotyped. A computational model can then be used to predict genetic variants that explain phenotypic differences across the panel.

QTL mapping has not previously been applied to bacteria, since the standard approach relies on sexual recombination during mating to break linkages between genetic variants. Since bacteria generally do not perform sexual recombination, there is no way to assess the effect of individual mutations.

SUMMARY OF THE DISCLOSURE

This disclosure provides a method for identifying quantitative trait-loci in bacteria comprising: providing two starting bacterial strains, wherein the two starting strains comprise compatible selectable genetic markers with each other; inducing at least two rounds of genomic recombination, wherein the at least two rounds of genomic recombination comprises (i) inducing a first round of genomic recombination between a population of a first starting strain and a population of a second starting strain to obtain first generation progeny bacteria, (ii) selecting among the first generation progeny bacteria to obtain two populations of bacteria that have undergone genomic recombination using two different selective media, wherein each selective medium kills both starting bacterial strains and allows only one of the two populations of the first generation progeny bacteria to live, (iii) inducing a second round of genomic recombination between one of the two selected populations of the first generation progeny bacteria and a population of bacteria that comprises a selectable marker compatible with the first selected population of the first generation progeny bacteria and that is selected from the group consisting of: (a) the other of the two selected populations of the first generation progeny bacteria, (b) a population of a strain that is otherwise genetically identical to one of the two starting strains, (c) a population of a strain that is different from both starting strains, and (d) a population of bacteria selected from progeny bacteria from genomic recombination between two different starting strains, thereby obtaining second generation progeny bacteria; (iv) selecting among the second generation progeny bacteria for two populations of bacteria that have undergone genomic recombination using two selective media, wherein each selective medium kills both populations of bacteria used in the second round of genomic recombination, and allows only one of the two populations of the second generation progeny bacteria to live, and (v) obtaining the selected two populations of the second generation progeny bacteria as two populations of a final generation progeny bacteria, or inducing at least one more round of genomic recombination and selection between a first selected population of the second generation progeny bacteria and a population of bacteria that comprises a selectable marker compatible with the first selected population of the second generation progeny bacteria; determining the sequences of the genomes of the two populations of the final generation progeny bacteria, thereby determining genetic variations within the genomes of the two populations the final generation progeny bacteria; determining at least one phenotype of the two populations of the final generation progeny bacteria; performing a population-wide analysis to identify genetic variations that associate with the at least one phenotype, thereby identifying quantitative-trait loci that are associated with the at least one phenotype.

In some embodiments, at least one of the two starting bacterial strains is a wild type strain and the other starting bacterial strain comprises at least two selectable markers wherein the at least two selectable markers are different from each other. In some embodiments, each of the two starting bacterial strains comprises at least one selectable marker, and wherein the at least one selectable marker of one starting bacterial strain is different from the at least one selectable marker of the other starting strain. In some embodiments, at least one of the starting bacterial strains is an auxotrophic strain. In some embodiments, at least one of the starting bacterial strains is an auxotrophic strain that is also resistant to a chemical. In some embodiments, at least one of the starting bacterial strains is a double auxotrophic strain. In some embodiments, at least one of the starting bacterial strains is a double auxotrophic strain that is also resistant to two different chemicals. In some embodiments, the at least one selectable marker comprises an antibiotic resistance gene. In some embodiments, the at least one selectable marker comprises an antibiotic resistance gene inserted into the bacterial genome to disrupt a gene essential for bacterial survival.

In some embodiments, the at least one phenotype comprises one or more of: bacterial growth rate, resistance to a chemical compound, production of a target biochemical, ability to transfer into new environmental niche, ability to persist in a new environmental niche, ability to modulate a host phenotype when established in the host microbiome, ability to inhibit growth of a target organism, and ability to grow under restrictive conditions.

In some embodiments, the genomic recombination at each round is achieved by protoplast fusion-induced homologous recombination.

In some embodiments, the bacterial strains used in the methods are Gram-negative. In some embodiments, the Gram-negative bacteria are selected from genera *Pseudomonas, Novosphingobium, Sphingobium, Sphingomonas, Escherichia, Zymomonas,* and *Cupriavidus*. In some embodiments, the genomic recombination of Gram-negative bacterial strains at each round is achieved by protoplast fusion-induced homologous recombination comprising (a) treating the Gram-negative bacterial strains with an antibiotic that inhibits peptidoglycan biosynthesis; and (b) inducing the treated bacterial strains to undergo protoplast fusion in a high osmolarity medium. In some embodiments, the antibiotic that inhibits peptidoglycan biosynthesis is Fosfomycin. In some embodiments, the high osmolarity medium comprises between 0.5 M and 1.2 M sucrose. In some embodiments, the protoplast fusion is achieved by chemofusion or electrofusion. In some embodiments, the chemofusion is achieved using polyethylene glycol.

In some embodiments, the bacterial strains used in the methods are Gram-positive. In some embodiments, the Gram-positive bacterial strains are selected from genera *Bacillus, Corynebacterium, Streptomyces, Propionibacterium, Clostridium,* and *Lactobacillus*. In some embodiments, the genomic recombination of Gram-positive bacterial strains at each round is achieved by protoplast fusion-induced homologous recombination comprising (a) treating the Gram-positive bacterial strains with lysozyme, and (b) inducing the treated bacterial strains to undergo protoplast fusion in a high osmolarity medium. In some embodiments, the high osmolarity medium comprises between 0.5M and 1.2M sucrose. In some embodiments, the protoplast fusion is achieved by chemofusion or electrofusion. In some embodiments, the chemofusion is achieved using polyethylene glycol.

In some embodiments, the population-wide analysis comprises: (a) mapping the sequences of each strain to the starting bacterial strains; and (b) determining the presence of single nucleotide polymorphisms and short insertions based on the mapping in (a). In some embodiments, the method further comprises (c) performing de novo assembly of genomes of each strain of the final generation progeny strains; and (d) determining large scale structural variants by comparing the assembled genomes of the final generation progeny strains to the genomes of the starting bacterial strains.

In some embodiments, the population-wide analysis comprises a variant calling step that comprise mapping the genotypes of the final generation progeny bacterial strains to the genotype of the starting bacterial strains. A variant calling step allows determining the differences (variations in the genome/variants) between the parents and the progeny bacteria, and also allows determining genomic contributions from each parent to the progeny bacteria.

In some embodiments, the population-wide analysis comprises a pruning step to cluster away variants that are in close genomic proximity to each other and have indistinguishable association to a given phenotype via a parameter sweep function that scans every variant as a potential start position for pruning.

In some embodiments, the population-wide analysis comprises a haplotype calling step. The haplotype calling of the instant disclosure scans for continuous sets of non-reference or non-individual specific variants to call haplotypes. In some embodiments, haplotype calling allows identifying regions of the genome that are prone to not recombine.

In some embodiments, the population-wide analysis comprises performing a Continuous Wavelet Transform Analysis.

DETAILED DESCRIPTION OF THE DISCLOSURE

Definitions

Figure 1A:
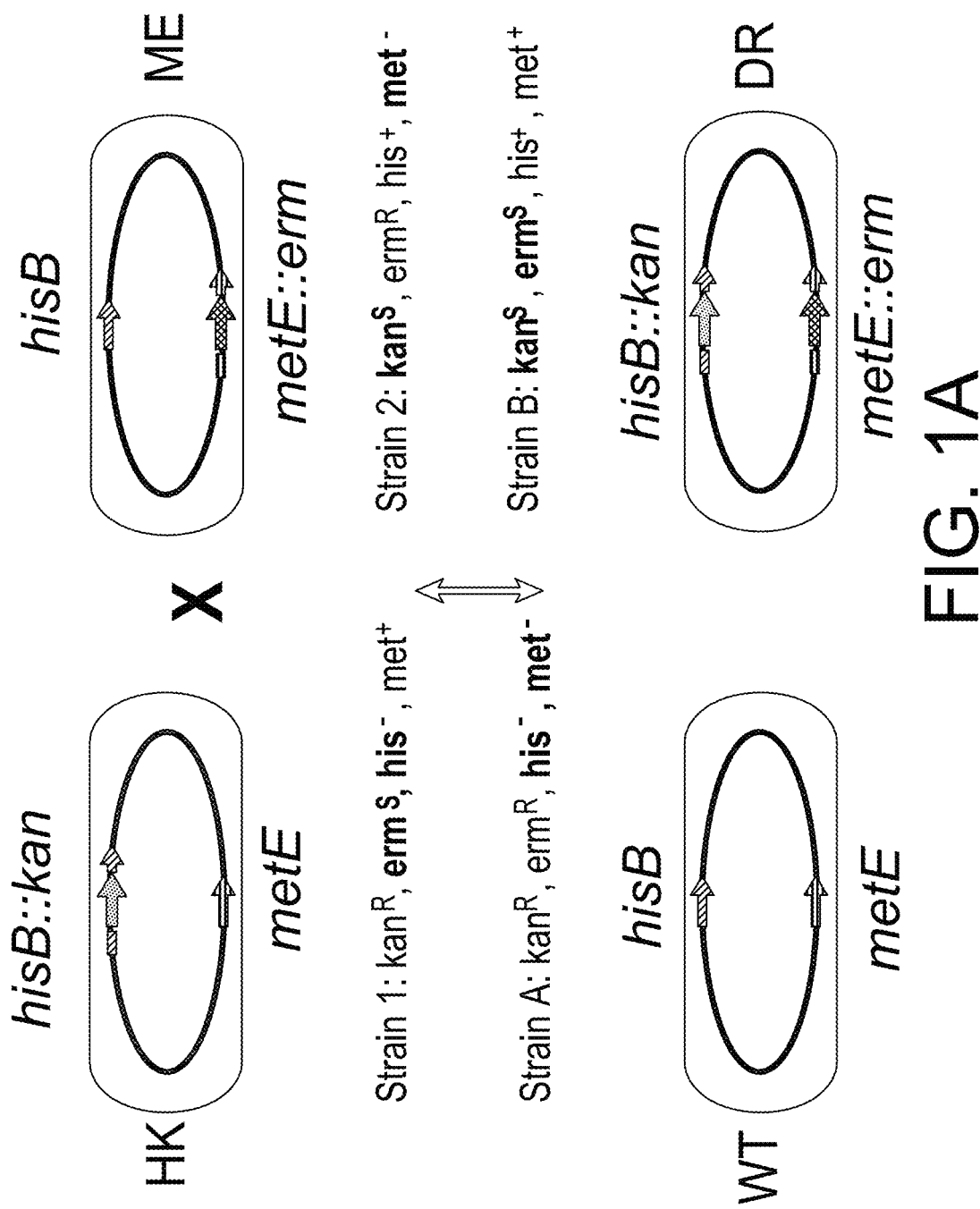
FIGS. 1A-1C. Analysis of genome shuffling in *Bacillus subtilis*. (A) Replacing amino acid biosynthesis genes with antibiotic resistance markers allows flexible identification of recombinant progeny following genome shuffling. (B and C) Crossing two parental (starting) strains, each with a different amino acid biosynthesis gene replaced by an antibiotic resistance marker, yielded prototrophic (B) and double resistant (C) progeny. Each concentric circle represents a different resequenced individual from this cross. The bars show sequences mapped to the 168 parent, with the remaining genomic sequence coming from the 3A27 parent. The arrows indicate locations of selection markers. Black arrows indicate the origin of replication. WT: wild-type; DR: double-resistant.

Unless defined otherwise, all technical and scientific terms used herein have the same meaning as commonly understood by one of ordinary skill in the art to which this invention belongs.

As used herein, the term "about" refers to an approximately +/−10% variation from a given value.

The term "auxotroph" refers to bacteria that lack the ability to synthesize at least one particular organic compound required for growth in a mineral salts growth medium with a simple carbon source such as glucose. The term "prototroph" refers to bacteria with the ability to synthesize all the compounds needed for growth in a mineral salts growth medium with a simple carbon source such as glucose.

The phrase "average nucleotide identity" refers to the extent of identity between the conserved coding regions across two genomes. Average nucleotide identity describes how similar two strains or species are to one another, i.e., the higher average nucleotide identity, the more similar the two strains or species being compared are.

The phrase "high osmolarity medium" refers to a medium with high enough osmolarity to prevent cell lysis from osmotic pressure. In some embodiments, the high osmolarity medium comprises at least 0.5M, at least 0.8M, at least 1M, at least 1.2M sugar. In some embodiments, the sugar is selected from sucrose, glucose or galactose. In a specific embodiment, the sugar is sucrose. In some embodiments, the high osmolarity medium comprises at least 0.5M, at least 0.8M, at least 1M, at least 1.2M salt. In some embodiments, the salt is NaCl.

The term "protoplast" refers to the entire cell, excluding the cell wall. Protoplasts can be generated by stripping the cell wall from bacterial cells by mechanical, chemical or enzymatic means.

The phrase "quantitative trait locus" (or "quantitative trait loci" for plural) (QTL) refers to a locus (i.e., location of DNA) and a group of loci that correlates with variation of a quantitative trait in the phenotype of a population of organisms. In some embodiments, QTLs are mapped by identifying which molecular markers (such as SNPs or AFLPs) correlate with an observed trait.

Bacterial Strains

The bacterial strains used in the instant methods are capable of having homologous (genomic) recombination with one another. Bacterial strains are capable of having homologous recombination with one another if they share a substantial degree of average nucleotide identity. In some embodiments, the parental bacterial strains used in the instant methods share at least 87% average nucleotide identity among conserved genes present in both parents. In some embodiments, the parental bacterial strains used in the instant methods share at least 90% average nucleotide identity. In some embodiments, the parental bacterial strains used in the instant methods share at least 92% average nucleotide identity. In some embodiments, the parental bacterial strains used in the instant methods are of the same species, i.e. the bacterial strains share at least 95% average nucleotide identity. In some embodiments, the parental bacterial strains used in the instant methods are of the same subspecies, i.e., the bacterial strains share at least 98% average nucleotide identity.

In some embodiments, the bacterial strains used in the methods of this disclosure are Gram-negative. In some embodiments, the Gram-negative strains are selected from genera *Pseudomonas, Novosphingobium, Sphingobium, Sphingomonas, Escherichia, Zymomonas*, and *Cupriavidus*.

In some embodiments, the bacterial strains used in the methods of this disclosure are Gram-positive. In some embodiments, the Gram-positive strains are selected from genera *Bacillus, Corynebacterium, Streptomyces, Propionibacterium, Clostridium*, and *Lactobacillu*.

Selectable Genetic Markers

As used herein, the phrase "selectable genetic marker" refers to a genomic feature in bacteria (e.g., the presence or existence of a gene, the lack of a functional gene, or a combination thereof), and that allows selection of the bacteria that contains or lacks the selectable genetic marker under restrictive conditions. "Selected bacteria" survive under the restrictive condition, while bacteria that do not survive will not be selected and therefore will not be "selected bacteria." In some embodiments, a "restrictive condition" contains a substance that is toxic/lethal to the bacteria against which the selectable genetic marker provides resistance. In some embodiments, a "restrictive condition" lacks a substance that the bacteria require/need for growth and that the selectable genetic marker provides.

In some embodiments, a selectable genetic marker simultaneously confers to a bacterium both resistance to a first compound and dependence on a second compound. In some embodiments, the dependence on the second compound is a result of disruption/inactivation of an essential gene of the bacterium. In some embodiments, the essential gene is chosen such that, under one set of conditions, the cells only survive if they have the wild type (functional) allele. Under a different set of conditions, the bacteria only survive if they have lost the wild type allele (or have a non-functional allele) because the bacteria are grown on media comprising a chemical that is nontoxic on its own but is activated to a toxic compound by the action of the enzyme encoded by the essential gene.

In some embodiments, the selectable genetic marker is an antibiotic resistance gene. In some embodiments, the antibiotic resistance gene confers the bacteria resistance to an antibiotic selected from the group consisting of kanamycin, ampicillin, chloramphenicol, erythromycin, lincomycin, streptomycin, gentamicin, amphotericin and penicillin.

In some embodiments, the selectable genetic marker can be a result of inserting an antibiotic resistance gene into the bacterial genome to disrupt/inactivate an essential gene—that is, two selectable markers are provided as a result of one genetic manipulation. In these embodiments, the bacteria comprising the antibiotic resistance gene also becomes auxotrophic for the product of the disrupted essential gene. Such bacteria can grow on a restrictive condition that comprises the antibiotic against which the antibiotic resistance gene provides resistance, but to survive, the bacteria also require the product of the disrupted essential gene to be supplied in the medium. In some embodiments, the disrupted essential gene is required for the synthesis of an amino acid, and the bacteria needs to be grown on medium that contains the missing amino acid.

The skilled artisan would also understand that different selectable genetic markers for resistance or auxotrophy can be used in place of the markers for resistance or auxotrophy used in the Examples of this disclosure.

Compatible Selectable Genetic Markers

The phrase "compatible selectable genetic markers" refers to selectable genetic markers in the two parental bacteria that allow selection for the progeny upon genomic recombination between the parental bacteria and against the parental bacteria. Parental bacteria can be a population of a bacterial strain (i.e., homogeneous in their genetic compositions), or can be a population (or a "pool") of progeny bacteria from a previous round of induced genomic recombination (therefore heterogeneous in their genetic compositions, except for one or more selectable genetic markers). In some embodiments, bacteria with compatible selectable genetic markers comprise a first strain or a first population that has no selectable genetic marker and a second strain or a second population with at least two selectable markers. In some embodiments, bacteria with compatible selectable genetic markers comprise a first strain or a first population that has at least one selectable marker and a second strain or a first population that has at least one selectable marker that is different from the at least one selectable marker in the first strain or first population.

In some embodiments, the following paired strains or populations would have compatible selectable genetic markers: (1) a wild type strain or population (prototroph and no resistance to any chemicals) (WT) and a double auxotroph/double resistant strain or population (DR), or (2) a single auxotroph strain or population that is also resistant to a chemical and another single auxotroph strain or population that is resistant to a different chemical, wherein each strain or population is auxotrophic for a different compound (i.e., needs a different compound to survive).

Protoplast Fusion

The methods of this disclosure utilize protoplast fusion-induced genomic recombination to break genetic linkages in bacterial genomes for QTL analysis. In some embodiments, protoplast fusion is achieved by stripping the outer cell wall of the bacteria, while leaving the inner cell membrane intact and inducing the bacteria to fuse and exchange genetic material by the help of a fusogen (a cell fusion facilitator/catalyst).

In some embodiments, the bacterial strain used in the methods of this disclosure is Gram-positive. In some embodiments, the Gram-positive bacteria are treated with lysozyme to remove the external peptidoglycan that usually surrounds the cell. The resulting bacteria without the cell wall are kept in a high osmolarity medium to prevent lysis during protoplast fusion facilitated by a fusogen. In some embodiments, the high osmolarity medium is a medium comprising between 0.5M and 1.2M sucrose. In some embodiments, the fusogen is polyethylene glycol (PEG).

In some embodiments, the bacterial strain used in the methods of this disclosure is Gram-negative. In some embodiments, the Gram-negative bacteria are treated with the antibiotic fosfomycin which inhibits peptidoglycan biosynthesis. In some embodiments, Gram-negative bacteria are treated with lysozyme with a chelating agent that destabilizes the cell wall and enhances access by the lysozyme. The resulting bacteria without the cell wall are kept in a high osmolarity medium to prevent lysis during protoplast fusion facilitated by a fusogen. In some embodiments, the high osmolarity medium is a medium comprising between 0.5M and 1.2M sucrose. In some embodiments, the fusogen is polyethylene glycol (PEG).

Genomic Recombination in Bacteria

Disclosed herein are methods for identifying quantitative trait-loci in bacteria (aka. "QTL mapping"). The inventors of the instant disclosure found that it is possible to break linkages between genes (which is necessary for QTL mapping) in bacteria through multiple rounds of protoplast-induced genomic recombination (aka. "homologous recombination" or "genomic shuffling"). In some embodiments, the multiple rounds of genomic recombination comprises at least 2 rounds, at least 3 rounds, at least 4 rounds, at least 5 rounds, at least 6 rounds, at least 7 rounds, at least 8 rounds, at least 9 rounds, or at least 10 rounds of genomic recombination. In general, the inventors have found that more rounds of genomic recombination result in finer resolution in QTL mapping.

In each round of genomic recombination, the bacteria that are subjected to protoplast-induced genomic recombination in that round are called the "parental bacteria" for that round, and the resulting bacteria are called the "progeny bacteria" or the "progeny." Unique to the present methodology, progeny bacteria are selected utilizing selectable genetic marker(s) to obtain progeny bacteria that have undergone successful genomic recombination, such that each subsequent round of genomic recombination uses the selected progeny (i.e., progeny that have undergone successful genomic recombination) resulting from the previous protoplast-induced recombination, as parental bacteria.

Protoplast-induced homologous recombination is an inefficient process, with only a small percentage (about 1%-5%) of the resulting progeny bacteria actually having undergone genomic recombination. The inventors have improved the efficiency and frequency of protoplast-induced genomic recombination by selecting successful recombinants after each genomic recombination, and using those progeny with successful recombinant as parents for the next round of genomic recombination. In some embodiments, selecting successful recombinant progeny is achieved by growing the bacteria in a restrictive growth medium that kills parental bacteria and allows the progeny bacteria that have had successful genomic recombination to survive.

In some embodiments, selecting progeny bacteria that have had successful genomic recombination ("successful recombinants") is achieved using a medium that kills parental bacteria and that allows only progeny bacteria that have successful undergone recombination to survive. In some embodiments, different restrictive growth media are used to select for successful recombinants with different properties.

In some embodiments, the parental bacteria used in the first round of genomic recombination (aka. the "starting strains") comprise at least one wild type strain. As used in, a "wild type bacterial strain or population" is not resistant to any chemical that is used for selection in the instant methods. As used in, a "wild type strain or population" is also a prototroph (i.e., self-sufficient and with the ability to synthesize all the compounds needed for growth, not an auxotroph).

In some embodiments, at least one of the starting strains has a pre-existing auxotrophy which is not associated with any resistance to any compound. In some embodiments, the pre-existing auxotrophy is for tryptophan, and the strain is grown on a minimal medium supplemented with tryptophan.

In some embodiments, the genomic recombination is between two bacterial strains or populations that comprise compatible selectable genetic markers with each other.

In some embodiments, one of the two bacterial strains or populations is double auxotrophic (i.e., a double auxotrophic bacterium lacks the ability to produce two different compounds necessary for survival and needs the two different compounds to be added to the minimal growth medium to survive), and is also resistant to two different chemicals. In some embodiments, the two different chemicals are two different antibiotics. In these embodiments, the other of the two bacterial strains or populations is a wild type (prototroph) bacterial strain or population, or a bacterial strain or population with a pre-existing auxotrophy with no associated resistance to any chemical. The expected result of a successful genomic recombination between a double auxotroph/double antibiotic resistant bacterial strain or population and a wild type bacterial strain or population is two progeny populations, both of which are single auxotrophs (needing addition of a single compound in the growth medium to survive) and resistant to a single chemical. The double auxotroph bacterial strain or population dies in a restrictive medium that only contains one of the two needed compounds, and the wild type bacterial strain or population dies in a medium that contains any antibiotic. In order to select for the two progeny populations that have undergone successful genomic recombination, the bacteria are grown on two different restrictive growth media—each growth media missing a compound and containing a single antibiotic.

In some embodiments, both bacterial strains or populations are single auxotrophs (meaning each bacterial strain is in need of a single compound to survive, wherein the compound needed by one bacterial strain is different from the compound needed by the other bacterial strain). In some embodiments, each single auxotroph bacterial strain or population is resistant to a chemical, wherein the chemical that one bacterial strain is resistant to is different from that of the other bacterial strain. In some embodiments, the chemicals against which the bacteria are resistant are antibiotics. The expected result of a successful genomic recombination of these single auxotroph/single resistant bacteria is either a wild type (prototroph and not resistant) bacterial population or a double auxotroph/double resistant bacterial population. Therefore, when grown on a restrictive medium that comprises the two different antibiotics and provides the two compounds that the double auxotroph bacteria cannot synthesize and need to survive, the parental bacteria and any wild-type progeny die as they are not resistant to both antibiotics, leaving only the double auxotroph/double resistant progeny. In a second restrictive medium, when bacteria are grown on a medium that does not supply any additional compounds (and also does not have any antibiotics), both of the parental bacterial strains and any double auxotroph/ double resistant progeny die because they each need at least one compound to survive, and only the wild type progeny survives.

Figure 5:
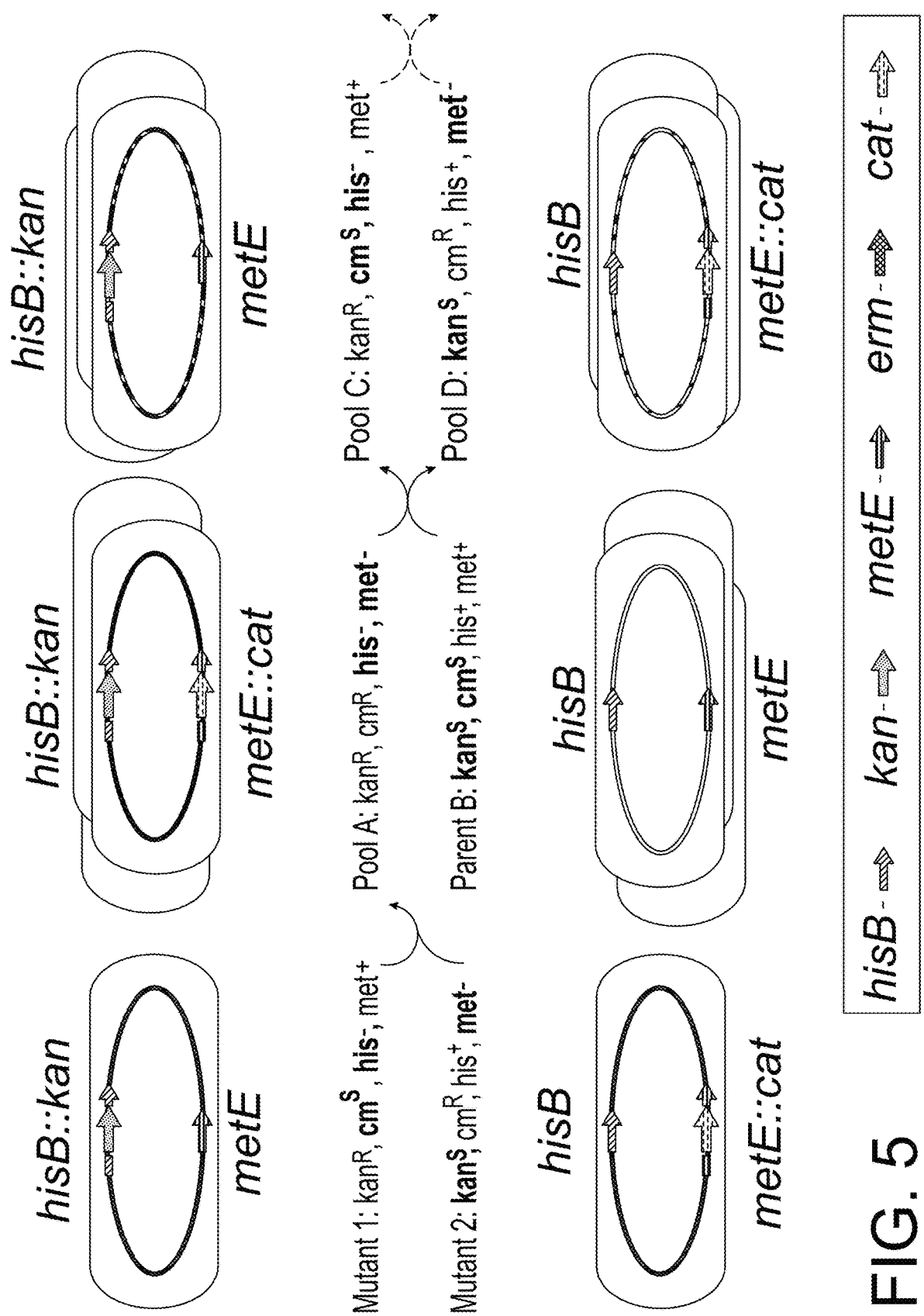
FIG. 5. A non-limiting exemplary representation of two rounds of genomic recombination (inbreeding).

A non-limiting exemplary embodiment for multiple (e.g., two) rounds of genomic recombination is shown in FIG. 5. In this non-limiting exemplary embodiment, the first parental bacteria (labeled as Mutant 1 in FIG. 5, aka "the first starting bacteria") comprises a single auxotroph that cannot synthesize histidine (his⁻) (thereby requiring histidine in the growth media to survive). The first parental bacteria also have a chloramphenicol (cm) resistance gene inserted into the hisB gene (thereby rendering the bacteria auxotrophic for histidine). The first parental bacteria can grow on chloramphenicol-containing media and requires histidine in the growth media. The second parental bacteria (labeled as Mutant 2 in FIG. 5, aka "the second starting bacteria") comprise a single auxotroph that cannot synthesize methionine (met) (thereby requiring methionine in the growth media to survive). The second parental bacteria also have a kanamycin (kan) resistance gene inserted into the metE gene (thereby rendering the bacteria auxotrophic for methionine). The second parental bacteria can grow on kanamycin-containing media and requires methionine in the growth media.

According to the example in FIG. 5, the progenies from the genomic recombination of the first and the second parental bacteria that have undergone successful genomic recombination are the following two populations. The first progeny population (labeled as "Pool A" in FIG. 5) is a double auxotroph/double resistant population which requires both histidine and methionine to survive, and has resistance to both chloramphenicol and kanamycin. A medium supplemented with histidine and methionine and further comprising chloramphenicol and kanamycin would select for this first progeny bacteria population with successful genomic recombination (the first parental bacteria would die because they are not resistant to kanamycin, and the second parental bacteria would die because they are not resistant to chloramphenicol). The second progeny population (labeled as "Pool B" in FIG. 5) is a prototroph/double sensitive population which does not require histidine or methionine supplementation to survive, but is sensitive to both chloramphenicol and kanamycin. A medium that does not have histidine, methionine or any antibiotic would select for this second progeny population with successful genomic recombination (since the first parental bacterial strain would die because the media lacks histidine, and the second parental bacterial strain would die because the media lacks methionine).

FIG. 5 also provides an example of a second round of genomic recombination. For this recombination, the successful progeny bacterial populations of the first round (labeled as "Pool A" and "Pool B" in FIG. 5) are used as the parents. One of the successful recombinant progeny bacterial populations of the second round of genomic recombination is a third progeny bacterial population (labeled as Pool C in FIG. 5) that comprises a single auxotroph that cannot synthesize histidine (his⁻) (thereby requiring histidine in the growth media to survive). The third progeny bacterial population also has a chloramphenicol (cm) resistance gene inserted into the hisB gene (thereby rendering the bacteria auxotrophic for histidine). The third progeny bacterial population can grow on chloramphenicol-containing media and require histidine in the growth media. The second progeny population resulting from the second round of genomic recombination is a fourth progeny population (labeled as "Pool D" in FIG. 5) that comprises a single auxotroph that cannot synthesize methionine (met) (thereby requiring methionine in the growth media to survive). The fourth progeny population also has a kanamycin (kan) resistance gene inserted into the metE gene (thereby rendering the bacteria auxotroph for methionine). The fourth progeny population can grow on kanamycin-containing media and require methionine in the growth media. It is noted that every other round, the resulting progeny has the same selectable marker phenotype as their grandparent strains (i.e., of two rounds before). In this instance, the progeny bacteria populations from the second round of genomic recombination have the same selectable marker phenotype as the original parental bacterial strains.

Non-limiting examples of different modes of genomic recombination are shown in FIGS. 6A-6D. The skilled artisan would understand and appreciate that, in order to attain a desired amount of genomic shuffling, it is possible to mix and match these modes of genomic recombination at each generation of recombinants.

Figure 6A:
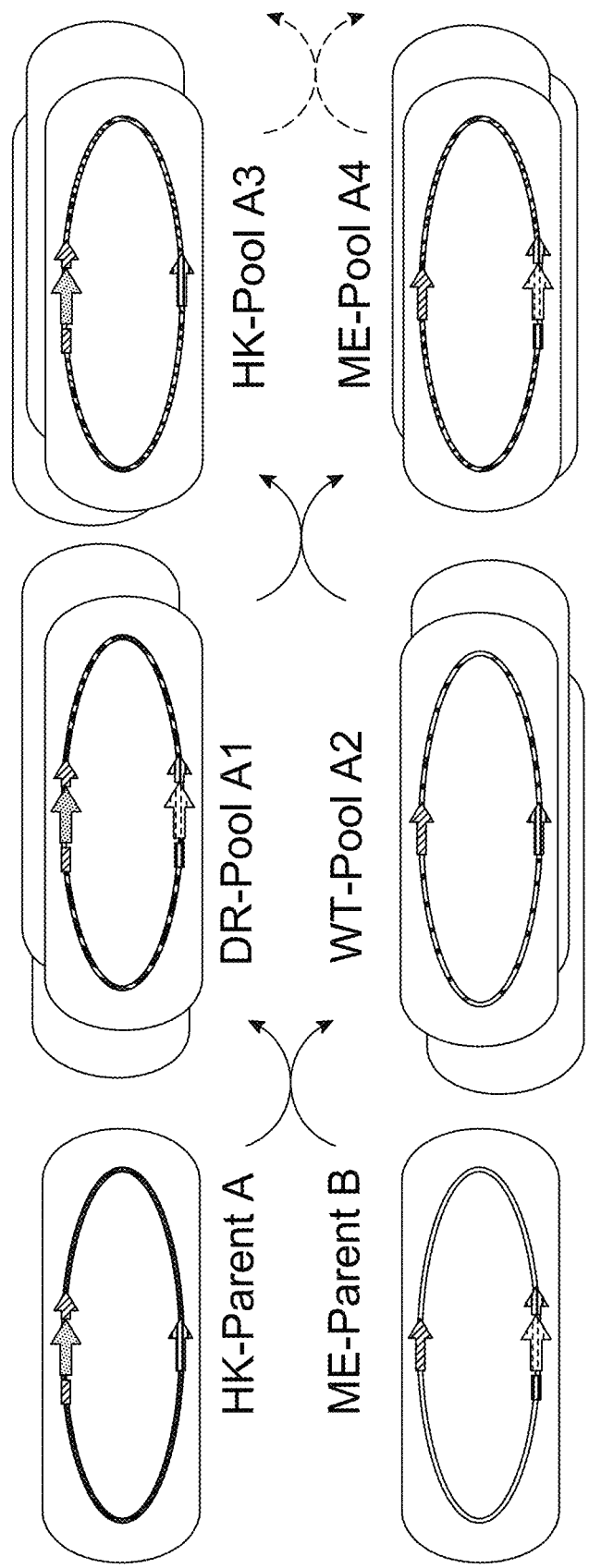
FIGS. 6A-6D. Non-limiting exemplary representations of different types of genomic recombination. (A) Inbreeding: progeny from one round are themselves shuffled for the next round. (B) Backcrossing: a population of progeny strains is induced to undergo genomic recombination with a population of a strain that is otherwise genetically identical to one of the two starting strains. (C) Diversification: a population of progeny strains is induced to undergo genomic recombination with a population of a strain that is different from both starting strains. (D) Lineage merger: a population of progeny strains from one genomic recombination is induced to undergo genomic recombination with a population of progeny strains from another genomic recombination. HK and ME stand for two different phenotypes of single auxotroph/single resistant bacterial strains. In this particular non-limiting example, HK bacteria are auxotrophic for the amino acid histidine and are resistant to the antibiotic kanamycin. ME bacteria are auxotrophic for the amino acid methionine and are resistant to the antibiotic erythromycin. DR stands for double resistant/double auxotroph bacteria. In this particular non-limiting example, DR bacteria are auxotrophic for both the amino acid histidine and the amino acid methionine, and they are resistant to both kanamycin and erythromycin.

FIG. 6A shows a non-limiting example of the "inbreeding" mode of genomic recombination where progeny of each round of genomic recombination are induced to undergo genomic recombination with each other. In FIG. 6A, the starting bacteria (either genetically homogenous "strains" or genetically heterogenous "populations" except for the selectable markers) are single auxotroph/single resistant (one starting bacterial strain (HK-Parent A) is auxotroph for histidine and resistant to kanamycin, while the other starting bacterial strain (ME-Parent B) is auxotroph for methionine and resistant to erythromycin. The first generation progeny bacterial populations resulting from these starting bacteria, which are either double auxotroph/double resistant (DR-Pool A1), or wild type (WT-Pool A2—prototroph and not resistant), are crossed with each other to obtain second generation progeny bacteria, both of which are single auxotroph/single resistant (HK-Pool A3 and ME-PoolA4).

Figure 6B:
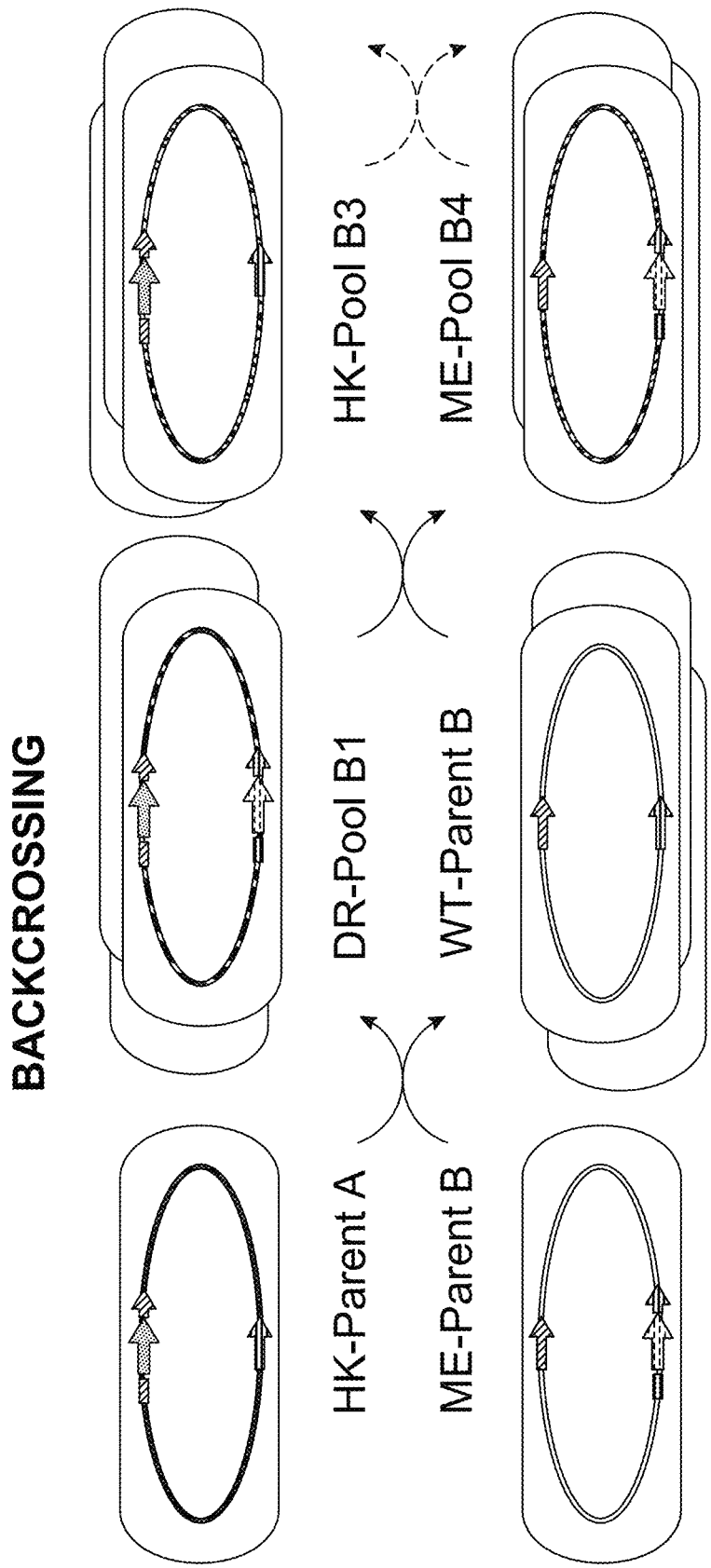

FIG. 6B shows a non-limiting example of the "backcrossing" mode of genomic recombination where one of the progeny of a genomic recombination round is induced to undergo genomic recombination with a parental bacteria (either genetically homogenous "strains" or genetically heterogenous "populations" except for the selectable markers) that has compatible selectable genetic marker. Backcrossing mode of genomic recombination increases the genomic contribution of the selected parental bacteria in the next generation progeny. In FIG. 6B, the double auxotroph/ double resistant (DR-Pool B1) first generation progeny bacterial population is backcrossed with a wild type (prototroph and not resistant) parental bacteria (WT-Parent B). The skilled artisan would also understand that, depending on which parent's contribution is desired to be increased, wild type (prototroph and not resistant) version of either parental strain can be used. Alternatively, in other embodiments, the wild type first generation progeny bacterial population can be backcrossed with a double auxotroph/double resistant version of either parental bacteria.

Figure 6C:
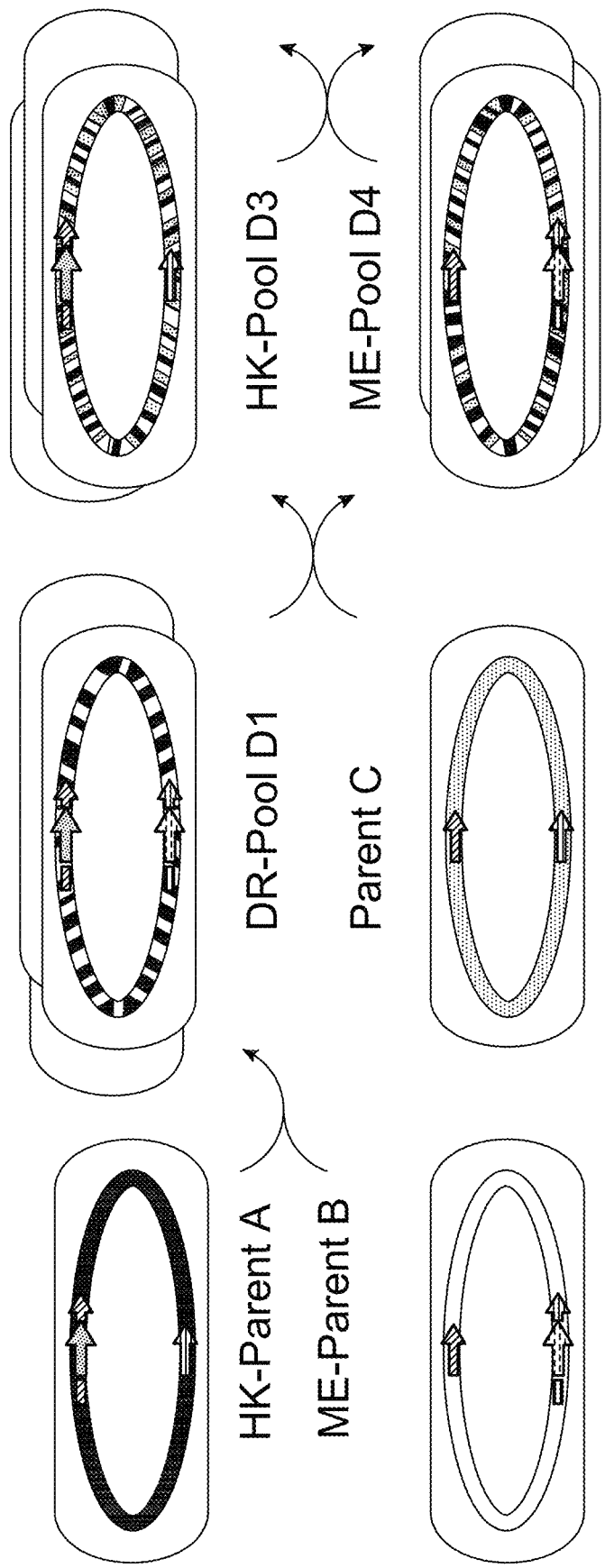

FIG. 6C shows a non-limiting example of the "diversification" mode of genomic recombination where one of the progeny of a genomic recombination round is induced to undergo genomic recombination with bacteria that is different from either of the parental (starting) bacteria and that has compatible selectable genetic marker. The diversification method allows diversification of the genomes of the resulting recombinant progeny.

Figure 6D:
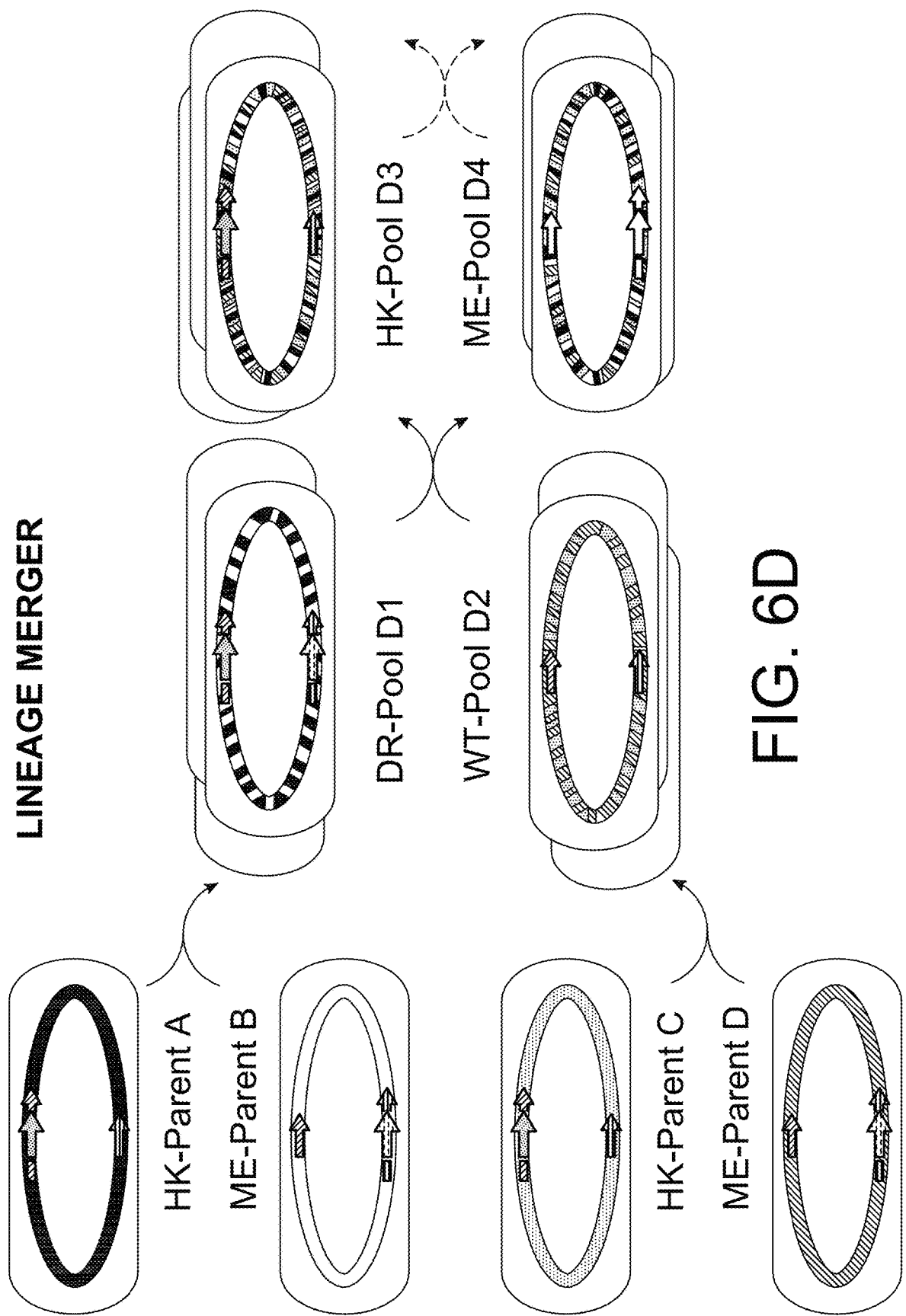
Figure 7A:
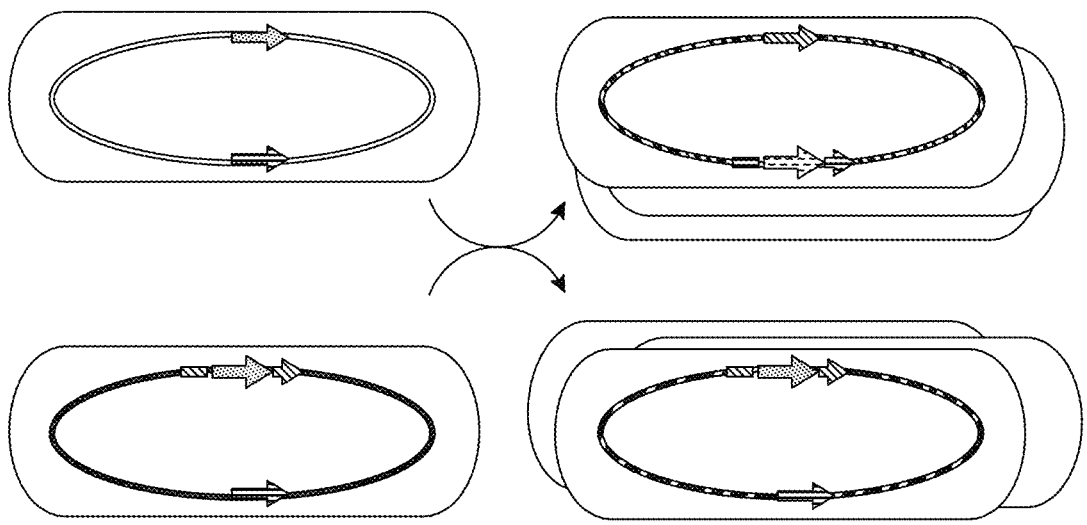
FIG. 7A-7E. A scheme of QTL mapping in bacteria. In eukaryotic genetic, QTL mapping is a powerful tool for identifying genetic variants that correlate with a phenotypic trait of interest. This approach has been difficult to apply to bacteria, since QTL mapping relies on sexual recombination to break linkages between genetic variants. The inventors overcame this barrier by (A) iterative genome shuffling to force homologous genome recombination between genetically-diverse bacterial cells. A single round of shuffling can produce dozens of random recombination events throughout the genome, and multiple rounds of shuffling decrease linkage further. (B) Shuffled strains are then arrayed in multiwall plates and sequenced. (C) The chimeric genomes are mapped to the original parents (starting strains). (D) Each strain is phenotyped. (E) Genetic variants that statistically correlate to quantitative phenotypic changes can be identified computationally, thereby identifying causal gene and variants.
Figure 7B:
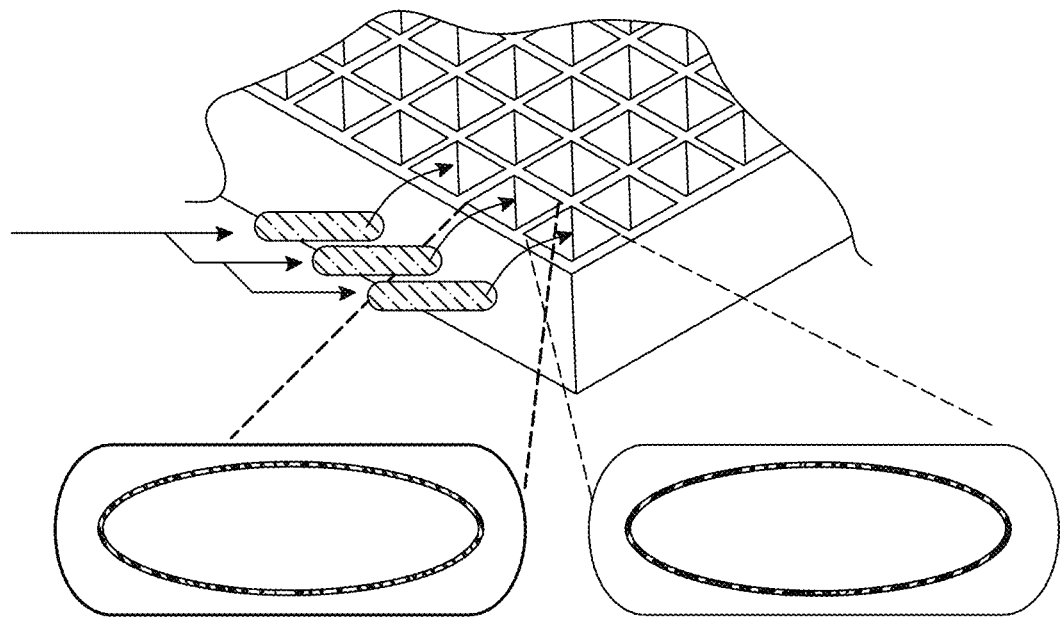
Figures 7C, 7D, 7E:
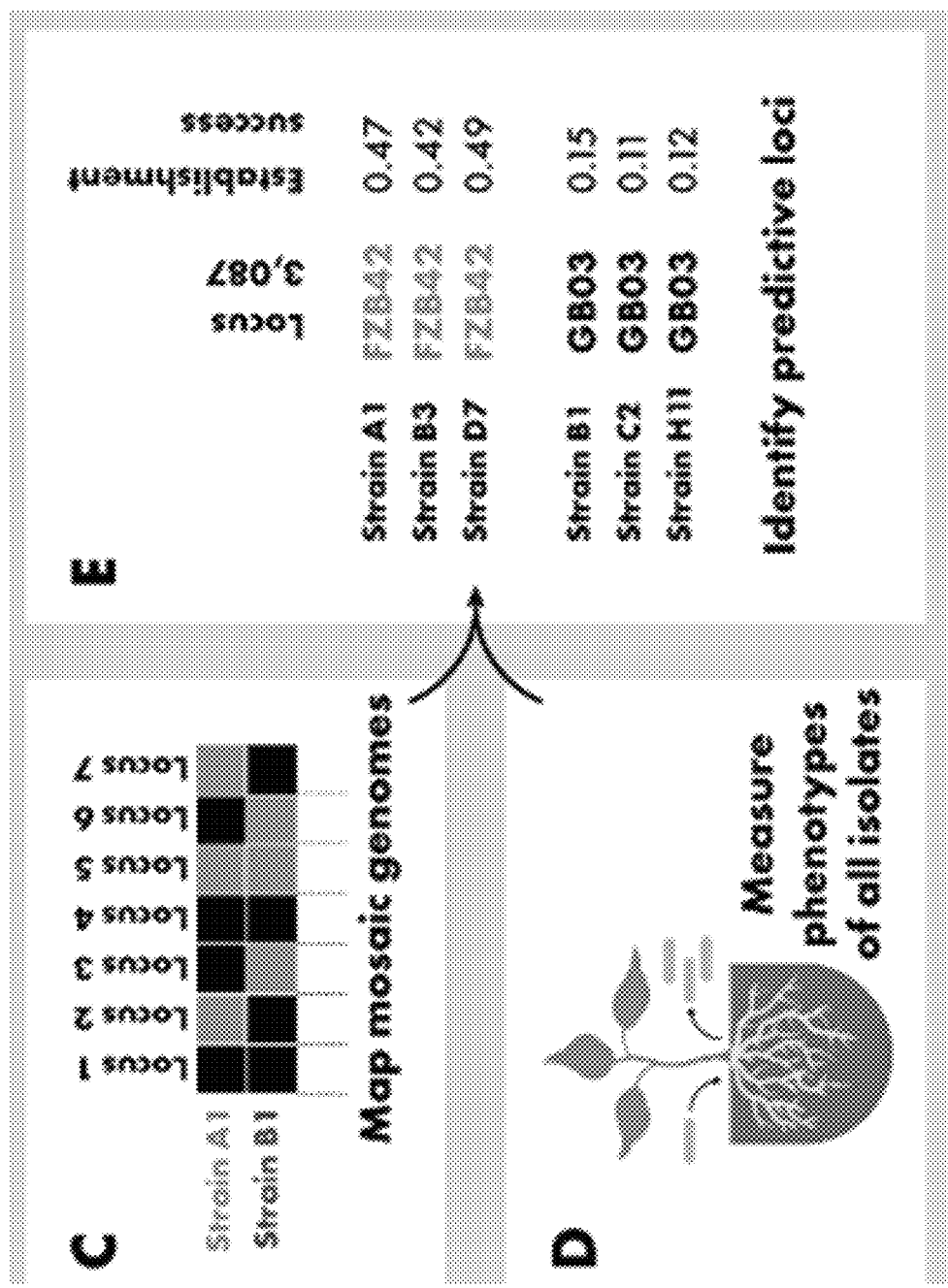

FIG. 6D shows a non-limiting example of the "lineage merger" mode of genomic recombination where one of the progeny of a genomic recombination is induced to undergo genomic recombination with a progeny of a different genomic recombination (e.g., a genomic recombination of different starting strains/populations). The lineage merger method allows having progeny that has genetic elements from more than two starting parental bacterial strains or populations. In FIG. 6D, the double auxotroph/double resistant (DR-Pool D1) first generation progeny bacteria of one genomic recombination is crossed with a wild type (prototroph and not resistant) first generation progeny bacteria of a different genomic recombination (WT-Pool D2).

In one aspect, the disclosure is directed to a method for identifying quantitative trait-loci in bacteria comprising: providing two starting bacterial strains, wherein the two starting strains comprise compatible selectable genetic markers with each other; inducing at least two rounds of genomic recombination, wherein the at least two rounds of genomic recombination comprises (i) inducing a first round of genomic recombination between a population of a first starting strain and a population of a second starting strain to obtain first generation progeny bacteria, (ii) selecting among the first generation progeny bacteria to obtain two populations of bacteria that have undergone genomic recombination using two different selective media, wherein each selective medium kills both starting bacterial strains and allows only one of the two populations of the first generation progeny bacteria to live, (iii) inducing a second round of genomic recombination between one of the two selected populations of the first generation progeny bacteria and a population of bacteria that comprises a selectable marker compatible with the first selected population of the first generation progeny bacteria and that is selected from the group consisting of: (a) the other of the two selected populations of the first generation progeny bacteria, (b) a population of a strain that is otherwise genetically identical to one of the two starting strains, (c) a population of a strain that is different from both starting strains, and (d) a population of bacteria selected from progeny bacteria from genomic recombination between two different starting strains, thereby obtaining second generation progeny bacteria; (iv) selecting among the second generation progeny bacteria for two populations of bacteria that have undergone genomic recombination using two selective media, wherein each selective medium kills both populations of bacteria used in the second round of genomic recombination, and allows only one of the two populations of the second generation progeny bacteria to live, and (v) obtaining the selected two populations of the second generation progeny bacteria as two populations of a final generation progeny bacteria, or inducing at least one more round of genomic recombination and selection between a first selected population of the second generation progeny bacteria and a population of bacteria selected from the group consisting of (aa) the other of the two selected populations of the second generation progeny bacteria, (bb) a population of a strain that is otherwise genetically identical to one of the two starting strains/populations, (cc) a population of a strain that is different from both starting strains/populations, and (dd) a population of bacteria selected from progeny bacteria from genomic recombination between two different starting strains/populations, thereby obtaining the final generation progeny bacteria; determining the sequences of the genomes of the two populations of the final generation progeny bacteria, thereby determining genetic variations within the genomes of the two populations the final generation progeny bacteria; determining at least one phenotype of the two populations of the final generation progeny bacteria; performing a population-wide analysis to identify genetic variations that associate with the at least one phenotype, thereby identifying quantitative-trait loci that are associated with the at least one phenotype.

In another aspect, the disclosure is directed to a method for identifying quantitative trait-loci in bacteria comprising: providing two starting bacterial strains, wherein at least one of the two starting strains comprises at least one selectable genetic marker; inducing at least two rounds of genomic recombination, wherein the at least two rounds of genomic recombination comprises (i) inducing genomic recombination between the two starting bacterial strains, (ii) selecting among first generation progeny bacteria for bacteria that have undergone successful genomic recombination using a medium that kills the starting bacterial strains based on the presence or absence of the at least one selectable genetic marker, (iii) inducing the selected first generation progeny bacteria to undergo a second round of genomic recombination, (iv) selecting among second generation progeny bacteria for bacteria that have undergone successful genomic recombination using a medium that kills the first generation bacteria based on the presence or absence of the at least one selectable genetic marker, and (v) obtaining the selected second generation progeny bacteria as the final generation progeny bacteria, or inducing the selected second generation progeny bacteria to undergo at least one more round of genomic recombination and selection, thereby obtaining final generation progeny bacteria.

In some embodiments, the method comprises three rounds of genomic recombination comprising: (i) inducing genomic recombination between two starting bacterial strains, (ii) selecting among first generation progeny bacteria for bacteria that have undergone successful genomic recombination using a medium that kills the starting bacterial strains based on the presence or absence of the at least one selectable genetic marker, (iii) inducing the selected first generation progeny bacteria to undergo a second round of genomic recombination, (iv) selecting among second generation progeny bacteria for bacteria that have undergone successful genomic recombination using a medium that kills the first generation bacteria based on the presence or absence of the at least one selectable genetic marker, (v) inducing the selected second generation progeny bacteria to undergo a third round of genomic recombination; and (vi) selecting among third generation progeny bacteria for bacteria that have undergone successful genomic recombination using a medium that kills the second generation bacteria based on the presence or absence of the at least one selectable genetic marker and selection, thereby obtaining the selected third generation progeny bacteria as the final generation progeny bacteria.

In some embodiments, the method comprises four rounds of genomic recombination comprising: (i) inducing genomic recombination between the two starting bacterial strains, (ii) selecting among first generation progeny bacteria for bacteria that have undergone successful genomic recombination using a medium that kills the starting bacterial strains based on the presence or absence of the at least one selectable genetic marker, (iii) inducing the selected first generation progeny bacteria to undergo a second round of genomic recombination, (iv) selecting among second generation progeny bacteria for bacteria that have undergone successful genomic recombination using a medium that kills the first generation bacteria based on the presence or absence of the at least one selectable genetic marker, (v) inducing the selected second generation progeny bacteria to undergo a third round of genomic recombination; (vi) selecting among third generation progeny bacteria for bacteria that have undergone successful genomic recombination using a medium that kills the second generation bacteria based on the presence or absence of the at least one selectable genetic marker and selection, (vii) inducing the selected third generation progeny bacteria to undergo a fourth round of genomic recombination; (viii) selecting among fourth generation progeny bacteria for bacteria that have undergone successful genomic recombination using a medium that kills the third generation bacteria based on the presence or absence of the at least one selectable genetic marker and selection, thereby obtaining the selected fourth generation progeny bacteria as the final generation progeny bacteria.

QTL Analysis

In some embodiments, the methods of the instant disclosure further comprise determining the genotypes of the final generation progeny bacteria. In some embodiments, the methods comprise isolating and sequencing genomic DNA from each final progeny bacteria that has successfully undergone genomic recombination. In some embodiments, determining the genotypes is achieved by whole genome sequencing of the final generation progeny bacteria. In some embodiments, the whole genome sequencing is achieved by next-generation sequencing.

In some embodiments, the methods further comprise determining genomic variation across a population of progenies. In some embodiments, determining genomic variation across a population of progenies comprises determining the genetic contributions in each strain from each of the parents as well as structural variants that may have occurred. In some embodiments, the structural variants comprise insertions, deletions, or rearrangements.

In some embodiments, the methods further comprise determining the presence of single nucleotide polymorphisms and/or short insertions and deletions. In some embodiments, determining the presence of single nucleotide polymorphisms and/or short insertions and deletions is achieved by sequence read alignment derived from each progeny bacterial strain genotype to the genomes of the original starting bacterial strains (i.e. the starting bacterial strains of the first genomic recombination).

In some embodiments, the methods further comprise determining larger structural variants. In some embodiments, determining larger structural variants is achieved by de-novo assembly of genomes of the progeny bacteria and comparing the resulting genomes to the genomes of the original starting bacterial strains.

In some embodiments, the methods comprise a variant calling step that comprise mapping the genotypes of the final generation progeny bacteria to the genotype of the original starting bacterial strains.

In some embodiments, the methods comprise a pruning step to cluster away variants that are in close genomic proximity to each other and have indistinguishable association to a given phenotype using a parameter sweep function that scans every variant as a potential start position for pruning. In some embodiments, the methods comprise pruning away variants that are in close genomic proximity to each other and have indistinguishable association to a given trait, thus their signal is considered linked. Pruning away linked variants can sometimes leave a single variant with substantial distance to the next representative variant even if distance is optimized. In some embodiments, the methods of the instant disclosure further comprise up and down weighting candidate variants that are associated to a given trait based on the variant density and uniformity across the genome. In some embodiments, weighting candidate variants helps flag the range of bases that have biological significance.

In some embodiments, the methods comprise a haplotype calling step. Haplotype calling in eukaryotes is a complex process that involves phasing markers connectivity to other markers to determine their position on two or more chromosome arms. Since prokaryotes are haploid there is no phasing required for haplotype calling in bacteria. The haplotype calling of the instant disclosure scans for continuous sets of non-reference or non-individual specific variants to call haplotypes. In some embodiments, haplotype calling allows identifying regions of the genome that are prone to not recombine.

Not all individuals inherit all genes from either parent and each parent is unlikely to carry the exact same gene content. Thus, in some embodiments, population level differential gene presence/absence is used as variants for the matching step.

In some embodiments, the methods comprise performing a Continuous Wavelet Transform Analysis to determine regions with low detectability of causative variants by scanning for local variant density.

In some embodiments, the methods of the instant disclosure further comprise determining at least one phenotype of the final generation progeny bacteria. In some embodiments, wherein the at least one phenotype comprises one or more of bacterial growth rate, resistance to a chemical compound, production of a target biochemical, ability to transfer into new environmental niche, ability to persist in a new environmental niche, ability to modulate a host phenotype when established in the host microbiome, ability to inhibit growth of a target organism, ability to promote growth of a target organism, and ability to grow under restrictive conditions.

In some embodiments, the methods of the instant disclosure further comprise associating the at least one phenotype to the genomic variation across a population of progenies; and identifying one or more quantitative trait-loci when variation in at least one genomic region has a statistically significant association to the at least one phenotype. With genomic recombination, genetic linkages between genes are broken, and progeny bacteria get a mix of parental genomes. Some phenotypes are affected by certain genetic elements (quantitative trait loci—QTL) of the parental bacteria. By matching the phenotypes to the resulting genomic variation, the instant methods identify the QTL or QTLs that are responsible for a certain phenotype in bacteria.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

EXAMPLES

Example 1

Materials and Methods

Strains and Chemicals.

Strains used in this work are summarized in Table 1. *Bacillus* strains were routinely grown in LB-Lennox at 37° C. and 250 rpm with antibiotic selection as appropriate. *Pseudomonas* strains were routinely grown at 30° C. and 200 rpm in LB-Miller with appropriate antibiotics. Antibiotics used include kanamycin sulfate (50 µg/ml), erythromycin (20 µg/ml) used in concert with lincomycin (12.5 µg/ml), gentamycin (25 µg/ml), and fosfomycin (800 µg/ml). *Bacillus* genome shuffling used SMM buffer (0.5 M sucrose, 20 mM magnesium chloride, and 20 mM maleic acid, pH 6.5) for protoplast formation, supplemented with 35% PEG 6000 and 10 mM calcium chloride for protoplast fusion (Schaeffer et al., 1976). *Pseudomonas* shuffling used Protoplast buffer (600 mM sucrose, 25 mM EDTA, 10 mM Tris-HCl pH 7.2) for protoplast formation, and Shuffle buffer (35% PEG 6000, 100 mM calcium chloride, 10 mM Tris-HCl pH 7.2) for protoplast fusion.

TABLE 1

Strains used in this disclosure.

| Strain | Genotype |
| --- | --- |
| B. subtilis subsp. subtilis 168 | trpC2 |
| B. subtilis subsp. subtilis RO-NN-1 | Wild-type |
| B. subtilis subsp. subtilis NCIB3610 | Wild-type |
| B. subtilis subsp. spizizenii TU-B-10 | Wild-type |
| B. mojavensis RO-H-1 | Wild-type |
| BKE13180 | 168 ΔmetE::erm |
| BKK34900 | 168 ΔhisB::kan |
| JMB1 | RO-NN-1 ΔhisB::kan |
| JMB3 | RO-NN-1 ΔmetE::erm |
| JMB5 | RO-NN-1 ΔmetE::erm ΔhisB::kan |
| Pseudomonas putida KT2440 | Wild-type |
| Pseudomonas putida S12 | Wild-type |
| KT2440 HK | P. putida KT2440 ΔhisH::kan |
| S12 HK | P. putida S12 ΔhisH::kan |
| S12 MG | P. putida S12 ΔmetE::gent |

Newly shuffled cells were plated on DM3 recovery medium (Chang and Cohen, 1979, Mol. Gen. Genet. 168, 111-115) or LB+0.01% bovine serum albumin. Recombinant *Bacillus* strains were subsequently plated on Spizizen minimal media (SMM) (Spizizen, 1958, *Proc. Natl. Acad. Sci. U.S.A.* 44, 1072-8). SMM plates were supplemented antibiotics as described above, and with tryptophan (400 µM), histidine (300 µM), and methionine (1 mM) as needed for various auxotrophic strains.

Strain Construction.

Strains BKK34900 (168 ΔhisB::kan) and BKE13180 (168 ΔmetE::erm) were provided by the BGSC (Koo et al., 2017). The allele replacement constructs were amplified from genomic DNA of these strains using primers hisB-FL/hisB-RL and metE-FL/metE-RL, respectively. Strain RO-NN-1 was then transformed with these PCR products by natural competence, following standard protocols (Koo et al., 2017, *Cell Syst.* 4, 291-305.e7. doi:10.1016/J.CELS.2016.12.013). Transformed strains were selected using LB containing the appropriate antibiotic and verified by colony PCR. Mutant strains were then resequenced as described below. A double mutant strain of RO-NN-1, containing both ΔhisB::kan and ΔmetE::erm, was constructed by genome shuffling as described below. This strain was then verified by whole-genome resequencing.

Strains KT2440 HK (KT2440 ΔhisH::kan), S12 HK (ΔhisH::kan), and S12 MG (ΔmetE::gent) were generated through standard double-crossover selection using pK18mobsacB and 400-bp regions of homology (Schäfer et al., 1994, *Gene*, 145, 69-73.).

*Bacillus* Genome Shuffling.

Cells for genome shuffling were grown in selective liquid media overnight, then diluted 100-fold the following morning. Once cultures reached an $OD_{600}$ between 0.4 and 0.6, 5 ml were pelleted by centrifugation for five minutes at 8000×g and washed three times in 1 ml SMM buffer. DNase (5 µg/ml) was added to the SMM buffer after initial wash steps. Protoplast formation was accomplished by resuspending washed cells in 1 ml SMM buffer with 1 mg/ml lysozyme and incubated at 37° C. for one hour. 500 µl of each parental cell line were mixed together after protoplasting and centrifuged for 20 min at 2000×g at 12° C. These mixed pools were washed once in SMM buffer, resuspended in PEG buffer, and incubated at room temperature for 20 minutes. Cells were again washed in SMM buffer and resuspended in 100 µl SMM buffer with 1% BSA added. Cells were then plated on DM3 regeneration media and incubated overnight at 37° C. Cells were scraped from regeneration plates the following day and plated to selective media for single colony isolation.

*Pseudomonas* Genome Shuffling.

Parental *Pseudomonas* strains were grown up overnight in 5 mL liquid LB media supplemented with their respective antibiotics at 30° C., shaking at 200 rpm. Saturated parental cultures were then each diluted 50-fold into 5 mL fresh liquid LB media+0.5 M sucrose+400 µg/mL fosfomycin, supplemented with their respective antibiotics, and grown at 30° C. shaking at 200 rpm for 3 hours until the OD reached 0.7-1.0. Each culture was then transferred to 100 mL of LB+0.5 M sucrose+800 µg/mL fosfomycin and incubated at 30° C. shaking at 200 rpm overnight. Each culture was then centrifuged (2000 rcf, 25° C., 15 min), resuspended in 1 mL Protoplast Buffer+100 µg/mL DNAse, and again centrifuged (3000 rcf, 25° C., 10 min). Cells were then resuspended in Shuffle buffer, incubated for 3 minutes at 30° C., washed once with 500 µL LB+0.5 M sucrose, resuspended in 200 µL LB+0.5M sucrose, and plated on regeneration plates Strain Isolation and Sequencing.

Individual strains were isolated either by plating serial dilutions or streaking to individual colonies on selective media. Single colonies were then picked and re-streaked to selective plates before being grown to saturation in selective liquid media. Genomic DNA was isolated using the Qiagen DNeasy Blood and Tissue Kit (Qiagen, Valencia, CA) according to the manufacturer's instructions. DNA for PacBio sequencing was isolated using the same method, but multiple samples were combined and concentrated to obtain higher concentrations. To achieve this, one tenth combined sample volume of 3M sodium acetate was added to pooled DNA, followed by 2.5× volume of 100% ethanol. This was mixed and incubated at −80° C. for 30 minutes. Precipitated DNA was then pelleted by centrifugation at 14,000 rpm for 20 minutes at 4° C., washed with 70% ethanol, and allowed to air dry. It was then resuspended in 1/10 TE and stored at −20° C. until being shipped on dry ice for PacBio sequencing.

For resequencing, Nextera XT libraries (Illumina, San Diego, CA) were generated from purified DNA of isolated strains according to the manufacturer's protocol (15031942 v03), stopping after library validation. Final libraries were validated on an Agilent Bioanalyzer (Agilent, Santa Clara, CA) using a DNA7500 chip and concentration was determined on an Invitrogen Qubit (Waltham, MA) with the broad range double stranded DNA assay. Barcoded libraries were pooled and prepared for sequencing following the manufacturer's recommended protocol (15039740v09, Standard Normalization). One paired end sequencing run (2×301) was competed on an Illumina MiSeq instrument (Illumina, San Diego, CA) using v3 chemistry.

Variant Calling

Fastq files from sequencing were first processed with Trimmomatic for phred base-pair quality. Reads that lost a paired read from phred filtering were removed. Reads that were shorter than 38 base-pairs were removed to reduce the quantity of non-uniquely mapping reads. Individuals were independently run through a variant calling pipeline using software current at the time the project started: BWA v0.7.17, Samtools v1.8, Picard v2.20.8, GATK v3.8.0, VCFTools v0.1.15, BCFTools v1.9, PLINK v1.9.0, and in-house R scripts (Li, H. and Durbin, R. (2009) *Bioinformatics*, 25, 1754-1760; Danecek, P. and McCarthy, S. A. (2017) *Bioinformatics*, 33, 2037-2039; Danecek, P. et al., *Bioinformatics*, 27, 2156-2158; Purcell, S. et al., (2007), *The American Journal of Human Genetics*, 81, 559-575; Li, H. et al., (2009), *Bioinformatics*, 25, 2078-2079; McKenna, A. et al., (2010), *Genome Res.*, 20, 1297-1303). Reads were aligned through BWA MEM to generate .sam files (Sam files). Samtools was then used to create compressed .bam files (Bam files) for further processing. Bam files were then parsed by samtools for uniquely mapping reads to a single locus, while multi-loci mapping reads were removed. Samtools was next used to order reads by their individual genome mapping coordinate and their read groups replaced. After removing non-mappable reads, and remaining reads ordered and properly annotated, bam files were scanned for duplicate calls with Samtools and then were indexed via Picard. Polished Bam file reads were run through GATK HaplotypeCaller with as haploids "-ploidy 1". BCFTools was used to filter low coverage variants, requiring a minimum read depth of 12 to confirm the variant. GATK's HaplotypeCaller function will only annotate the most common variant in haploid organisms, and since sequencing errors are rare, only variants with several reads (20≥) are marked in VCF files. Variants were also BCFTool filtered for a genotype quality of $p<0.1\times10^{-6}$ to ensure the chance of a false variant was less than 1:100,000 chance. A random subset of individuals was then scanned by eye to check for variants in low coverage areas, that no low-coverage variants were marked, and no biallelic states were present. Final bioinformatic analysis was done in R v3.5.0 using Plink ped/map file format.

Genomic Feature Analysis

Parent A/B Detection and Filtering

Within each shuffled population variants were first called against each parent reference genome. However, in every recombinant population the parent strain 3A27 remained the dominant contributor to offspring genomes, thus was used for all further variant calling and genome analysis. In each population variants were encoded as "0" for 3A27, and "2" as the recessive parent. Variants called in both parents at a single position are likely sequencing errors that arose during laboratory processing or DNA sequencing. Markers not present in at least one offspring were also removed. Any variant found in one parent and one individual were kept for recombination and insertion analysis methods. Lists for differential variants between parents were used for permutation testing (mentioned below).

Insert Size and Amount Quantification

Each shuffled population is composed of bi-parental crosses thus progenic strains are composites from two parents. Post variant encoding, insert size was calculated based on the number base pairs between continuous variants from the recessive parent. Each parent combination has varying shared identity, thus the resolution to detect the exact position of recombination is parent and loci specific ranging from 1 in 50 bases (98% identity) to 1 in 8 bases (87% identity). The positions and lengths of insertions from recessive parents were calculated for each individual. Variant positions are fixed to genomic differences between parents, thus frequencies of specific variants across individuals were used to show what regions had higher and lower recombination across shuffled population members. Population features and shuffling was visualized by the R package 'BioCircos' and standard plotting libraries (Cui et al., 2016, *Bioinformatics*, 32, 1740-1742). The quantity of insertions per strain was similarly quantified by totaling each individual's strings of recessive markers.

Population Level Genome Feature Analysis

Read mapping statistics were calculated using VCFTools and the 3A27 reference genome as the dominant parent (Danecek et al., 2017, *Bioinformatics*, 27, 2156-2158.). Read depth per shuffle was calculated using '—depth' for population level read depth. Likewise, VCFTools function "—mean-depth" was used for broad read depth, and '—site-depth' was used for variant sequence depth per individual in each shuffle. Site mean depth was calculated by VCFTools '—site-mean-depth' function to get per sample mean sequence depth.

Permutation Testing Against Genome Features

Recombined positions in the genome were examined against other extractable genomic features. IGV v2.3.5 was used for genomic feature extraction of a known methylation motif (GAYGNNNNNNCTT) (SEQ ID NO: 1) and GC content (Robinson et al., 2017, *Computational Exome and Genome Analysis*, 10.1201/9781315154770-17). Additionally, known gene positions within the dominant reference parent 3A27 were also used in testing variants involved in insertion detection. In each permutation test a two stage random number generator was used; the first seed number to create a list of random numbers, that was then used to create a second set of random numbers each used once in a single iteration within tests. In each test, positions of population features were compared to randomly generated lists of genomic positions to test if insertions between parents have statistical significance to SNPs/variants, methylation motifs, or GC content. Each test was run against 10,000 randomly generated subsets to create a p-value significance level of 0.0001. Iteration subsets of random test positions were based on the number features detected. For instance, 1,066 methylation motifs exist in the 3A27 genome, thus per each iteration 1,066 random positions were used.

Methylation to Insertion Testing

To investigate if methylation sites are closer than random to insertion sites the inventors compared "distance in base pairs from methylation motifs to random positions" to "base pair distance of motifs to insertion sites". A list of randomly generated genome positions was created to draw subsets per iteration equal to the number of insertion events per population. In each iteration, the distance to a methylation was calculated to a randomly drawn genome position to create a distribution of randomly drawn base pair lengths. Then, subsets of our 1,066 known methylation motifs were drawn per iteration and base pair distance was calculated to the nearest 5' or 3' end of an insertion event. The distributions were also calculated for normality using the Shapiro-Wilk tests if distributions are parametric or non-parametric. The mean and standard deviation were also compared with T-tests, F-tests, Wilcoxon-Tests, and Kolmogorov-Smirnov tests for significance.

Gene Position Permutation Testing

Similar to the methylation motif testing, insertion events across the population were tested for distance to gene start-stop positions (coding regions) in either the 5' or 3' direction. A randomized list of test positions was generated based on the number of insertion sites in the whole population, each iteration had a unique equally sized subset of random positions. The distributions of distance to random positions and insertion positions were also compared with T-tests, F-tests, Wilcoxon-Tests, and Kolmogorov-Smirnov tests for significance. The distributions were then calculated for normality using the Shapiro-Wilks test.

Insertion Events to Random Position Testing

Insertion events could be biased toward specific positions within the genome. To test this, the inventors generated two lists of random genome positions and calculated base pair distance between pairs of positions, for each random position in data set one, find the distance to the closest randomly drawn position in the second random set. Then the inventors randomly drew positions in the genome and calculated distance to the nearest 5' or 3' insertion event and compared the two distributions with the same metrics featured in other tests within this study.

GC Content Permutation Testing

Approximately 46% of the *B. subtilis* genome is G or C, thus proximity in bases to the nearest G or C is not meaningful. Two similar tests for GC content correlation to insertion positions were implemented. One test examined uni-directional outward GC content away from insertion sites; from the 5' insertion then examining increasing windows beforehand (3' to 5'), and the 3' end of the insertion expanding forward (5' to 3'). GC content was measured by percent GC at increasing increments through exponentially increasing windows of $2^n$ bases, n=2:12 ($2^2$ from $2^{12}$; 4 bases to 4,096 bases). The same test was performed on randomly generated insertions, unique to each iteration, and the percent GC was calculated using the same exponential scan pattern as variants. To generate a list of random insertions with comparable insertion lengths, random markers were chosen from a list of known variant sites between the two parents as the 5' end. To get a comparable 3' marker as the insertion switch point, actual insertion sizes were randomly drawn and assigned to 5' variants and the closest 3' differential variant was chosen in either direction, thus creating the most similar possible insertion size to an observed insertion size. To generate in-silico variants required the use of the R package "ecodist" (Goslee et al., 2007, *Journal of Statistical Software*, 22). A very similar test was performed scanning GC content, but in both κ' and 3' directions from insertion ends (scanning away and into the insertion markers). A smaller set of windows was used since the chance of double counting GC content exists within the boundaries of in-silico simulated insertions. When building simulated insertions, insertion sizes that were smaller than 1024 were removed. Thus, window sizes considered ranged from $4^n$, n=1:4 (4 bases to 256 bases). Limiting the GC content scan within insertion sites to 256 bases means that up to 50% of the insertion site was scanned for % GC content.

Wavelet Analysis for Population Features and a Range of Complexities

Wavelet transforms can analyze signal-based data by expanding 2 dimensional data into 3 dimensional space at varying scales to reveal otherwise cryptic patterns. The underlying theory of wavelet analysis is to overlay an organized specific wave of designated length and area over a signal series to find differences in area annotated as coefficients. Wavelets can find patterns or quantify "how much of a peak" is present at a region of a signal that is not immediately obvious to the human eye, and scanned at varying scales/window sizes of data (Spencer et al., 2005, *PLoS Genetics*, e148, Weighill et al., *Adv. Biochem. Eng. Biotechnol.*, 160, 143-183). Within this study the inventors implemented a Continuous Wavelet Transform (CWT) using the Ricker Wavelet as the mother wavelet to identify regions of the genome with differing characteristics of recombinant loci and potential hot and cold locations across strain populations. Ricker wavelets are ideal for this scan type since they target one specific location relative only to immediate up and downstream signal, being they are composed of three parts with a total area of zero (two negative peaks with area=−0.5 flanking a single positive peak with area=1).

Below is the wavelet transform that returns the wavelet coefficients W(s,τ) that are calculated across scales (s) and translation along the genome as τ (shifts across the x-axis) (Leavey et al., 2003, *Insight—Non-Destructive Testing and Condition Monitoring*, 45, 344-353.).

$$\psi(t) = \frac{2}{\sqrt{3\sigma}\,\pi^{1/4}}\left(1 - \left(\frac{t}{\sigma}\right)^2\right)e^{-\frac{t^2}{2\sigma^2}}$$

The resulting coefficients will indicate at specific scales the quantity of peak present. Wavelet analysis was performed using the R statistical programming language 3.5.0 and the package 'wmtsa' specifically was used for wavelet transform analysis (Constantine et al., 2001, *Phys. Rev. E Stat. Nonlin. Soft Matter Phys.*, 64, 036301; R: The R Project for Statistical Computing). Genomic data is encoded as "0" and "2" and only for relevant positions such binary transition states collapsed only to varying positions doesn't lend well to signal processing, thus variant data was modified in two ways (Weighill et al., 2017, *Adv. Biochem. Eng. Biotechnol.*, 160, 143-183). First, all variant positions were summed across the population to a single vector and spread out to their actual position, where absence of a variant was annotated as a zero. Secondly, data was binned down to approximately 4,010 data points (100× reduction) depending on the genome marker positions of each population. Once the data was transformed to amenable wavelet analysis qualities the locations with differing areas to the mean with either higher or lower than expected values were revealed.

SNP Analysis.

Strain reads were aligned against the reference genome using an in-house developed pipeline to call variants for SNPs and Indels. Paired end fastq files were first aligned against respective reference genomes using the BWA-MEM alignment tool to generate .sam files (Li, 2013, arXiv: 1303.3997v1 [q-bio.GN]). Before samtools was used to convert to bam format, sam files were examined for reads that are non-uniquely mapping (mapping to more than one loci) and were removed from analysis via AWK regular expression to remove reads with low mapping quality. Post samtools conversion to bam, bam files were sorted and re-aligned to validate variants using common methods in picard tools and genomic analysis tool kit (GATK) from the Broad Institute (Li, 2009, *Bioinformatics*, 25, 2078-9). Once .bam files were refined, they were converted to variant call format (.vcf) for individual samples through the GATK HaplotypeCaller function, then markers were validated using the same software's ValidateVariant function. VCF files were then compressed using bgzip and tabix and sent to BCFTools for merging of multiple VCFs across samples using the GNU parallel software (Tange, 2011, *The USENIX Magazine*, February 2011:42-47).

QTL Analysis.

The current association method to be implemented can be represented by the following univariate equation mixed model equation:

$$y=W\alpha+x\beta+u+\varepsilon; u\sim MVNn(0,\lambda\tau-1K),\varepsilon\sim MVNn(0,\tau-1In)$$

Quantitative traits are represented by vector y for n individuals. Individuals n by c (c=a matrix of covariates) represent fixed effects as W ($w_1, \ldots, w_c$). Alpha ($\alpha$) is a vector derived from covariates as corresponding coefficients. The vector x is derived from individuals as genetic markers (genotypes) and $\beta$ is the effect size of said genetic marker. When and likely needed, $\varepsilon$ denotes a vector of errors derived from population, u accounts for random effects, and $\varepsilon$ represents the variance of residual errors. K is used to account for relatedness across the population which can be derived from either PCA or a pairwise genomic relationship matrix. I. is a population based identity matrix and MVN, is a multivariate normal distribution. This equation is derived from GEMMA. The inventors believe that bacteria will have different random effects than typically seen in Eukaryotes, so a few alternative equations can be used as needed:

$$y=W\alpha+x\beta+u+\varepsilon; u\sim bMVNn(0,\lambda\tau-1K),\varepsilon\sim MVNn(0,\tau\sim 1In) \quad A:$$

$$y=W\alpha+x\beta+u+\varepsilon; u\sim MVNn(0,\lambda\tau-1K),\varepsilon\sim bMVNn(0,\tau-1In) \quad B:$$

$$y=W\alpha+x\beta+u+\varepsilon++b; u\sim MVNn(0,\lambda\tau-1K),\varepsilon\sim MVNn(0,\tau-1In) \quad C:$$

The equations are similar to the above, but the difference is a metric b where bacteria shuffling effects are taken into account in random effects or error effects. Since patterns of recombination vary in hot and cold spots along the genome, the proximity to shuffling increases the chance of marker association. The inventors created a system to account for how uniform shuffles are across the genome by examining evenness of shuffling to LD pruning. The more even the LD pruning and shuffles are to each other the more likely a trait specific locus can be detected. A vector b derived from the amount of shuffling within LD flagged parts of the genome as b=2×(gF) where a vector of genotypes x are weighted by their proximity to a highly recombinant region F and scaled to 0-1 by a variance of g which is the mean number of bases to the leading and lagging strand nearest LD derived flags based on the variance of bases between all flags. The vectors are then multiplied by two to create either an up or down weighting to each marker and can be part of either u or c as in equations A and B. The alternative is that b can be part of the linear model as a separate additive effect as in equation C. These models take into account the amount of recombination along the genome in the study set of individuals and the amount of local recombination of each marker (FIG. 1). This can also be applied to multivariate linear mixed models.

Example 2: Iterative Genome Shuffling Breaks Linkages Between Genes

Successful genome shuffling is typically assessed through simultaneous selection for two markers, one from each parent. To make this strategy more flexible, the inventors replaced biosynthetic genes that are essential for growth in minimal media with antibiotic resistance markers (FIG. 1A). This approach allows selection for any of the four potential allele combinations. In *Bacillus subtilis*, the inventors chose hisB and metE as biosynthetic genes, since these gene deletions produce defined auxotrophies (Koo et al., 2017, *Cell Syst.* 4, 291-305.e7) and the genes are roughly opposite from one another in the circular genome, separated by 2.2 and 2.0 Mb.

A single round of shuffling can introduce roughly 40 segments of DNA, ranging in size from less than 100 nbp to tens of kbp. Multiple rounds of shuffling can be used to further increase recombination between the parents.

To determine the genome-wide effects of protoplast fusion, the inventors performed reciprocal crosses of 168 ΔhisB::kan ("168 HK")×RO-NN-1 ΔmetE::erm ("3A27 ME") and RO-NN-1 ΔhisB::kan ("3A27 HK")×168 ΔmetE::erm ("168 ME"). Recombinant strains containing either both mutant alleles (ΔhisB::kan ΔmetE::erm, "DR") or both wild-type alleles (his$^+$ met$^+$, "WT") were then selected. Eighteen recombinant strains from each combination of shuffle and selection were isolated and sequenced using short-read sequencing. The 168 HK×3A27 ME prototrophic pool was contaminated by other prototrophic isolates and therefore was not analyzed further. To identify large-scale genome rearrangements, two parental and four recombinant strains were sequenced using long-read-sequencing.

Figures 1B, 1C:
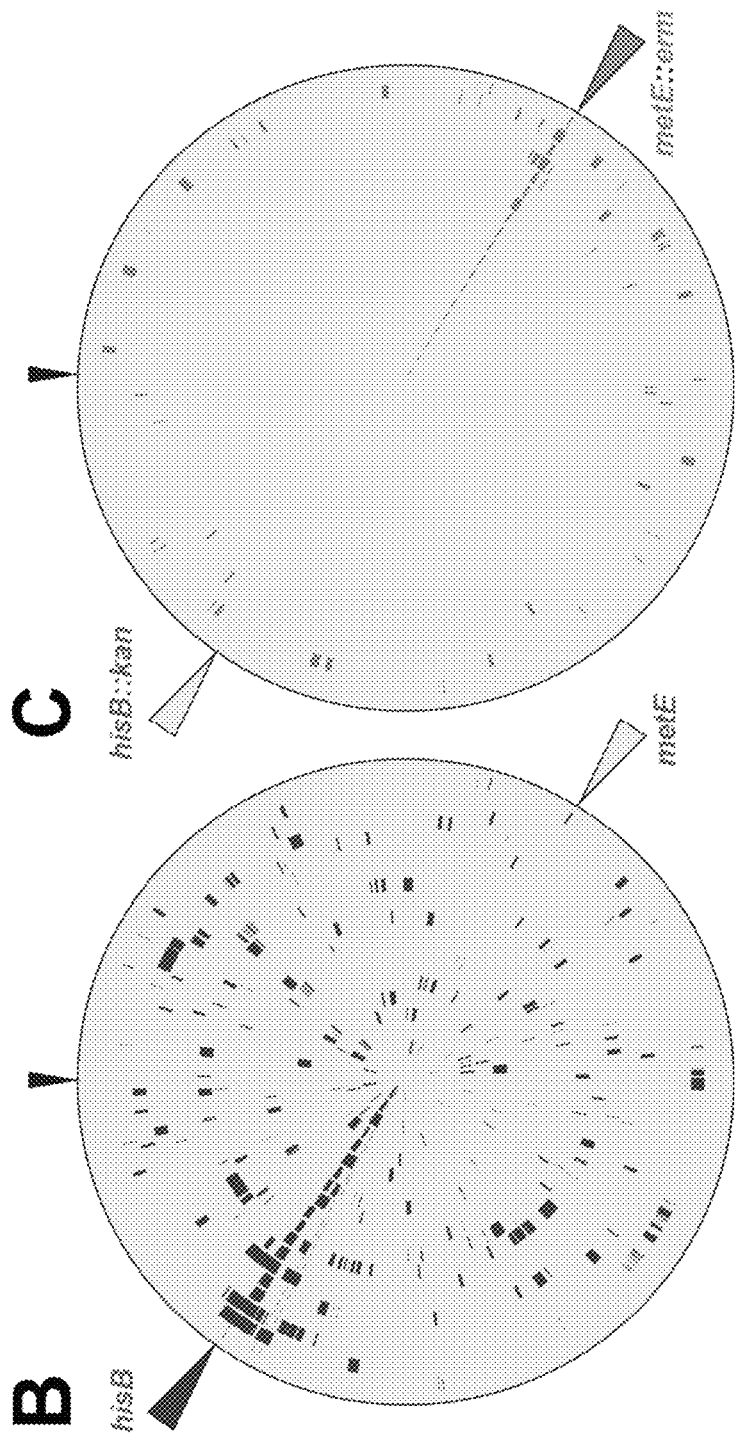
Figures 2A, 2B:
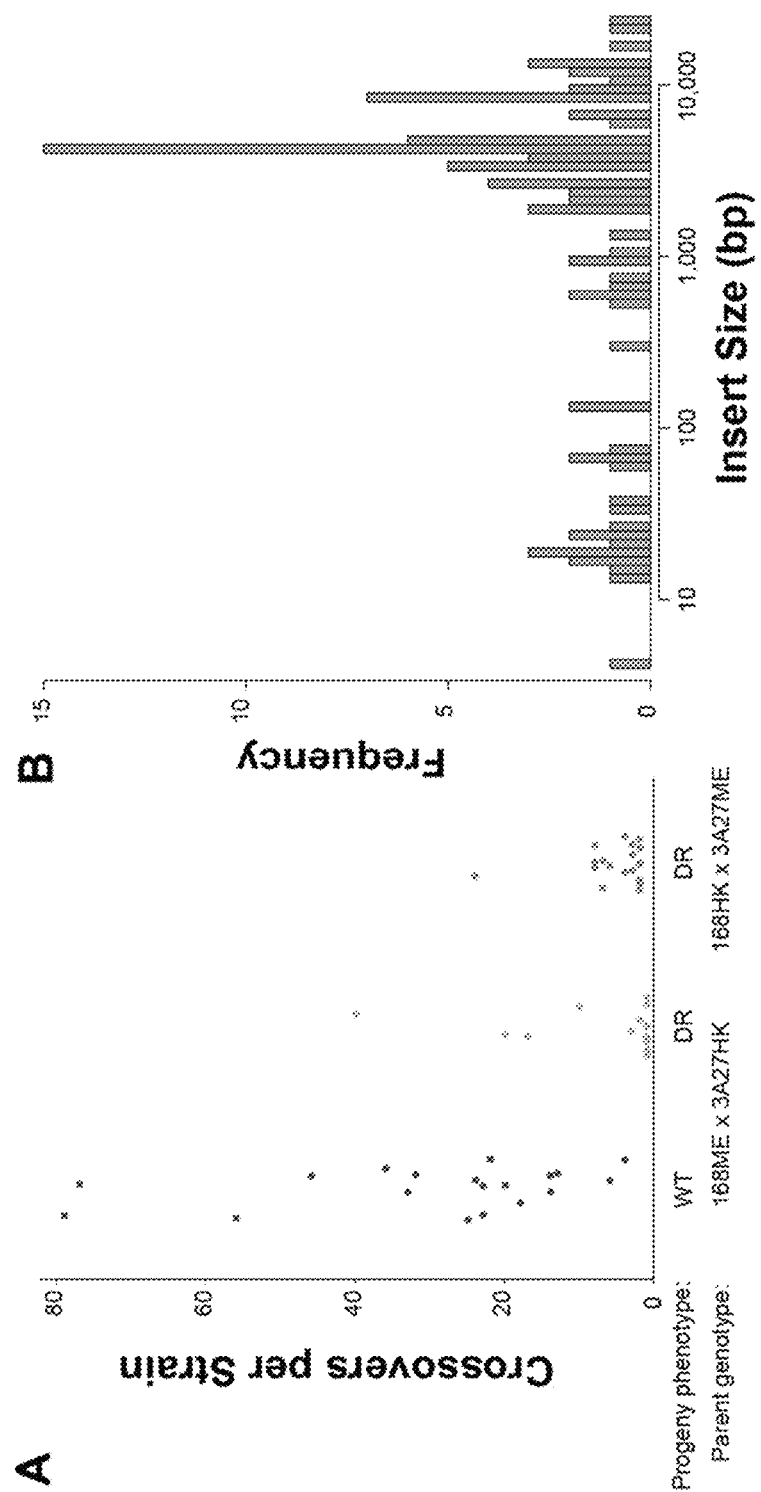
FIGS. 2A-2B. Analysis of recombination frequency and size. (A) The number of recombination events was calculated for each strain in a given pool, representing each strain by a single data point. (B) Combining all recombination events from the three characterized pools shows [a broad distribution of sizes]. WT: wild-type; DR: double-resistant.

The chromosomes of 168 and RO-NN-1 strains contain abundant SNPs which allow identification of genomic regions inherited from each parent in the recombinant strains with high accuracy. Sequencing results revealed a strong asymmetry in recombination, with one of the parental strains (3A27 ME or 3A27 HK) contributing the predominant portion of the chromosome of the progeny (FIG. 1B and FIG. 1C). All recombinant strains carried the selected marker flanked by different amounts of DNA originating from the second parent (168 HK or 168 ME). In addition, the inventors detected extensive un-selected variation across their genomes with multiple unrelated regions of recombination. Individual WT recombinant chromosomes contained up to ~80 separate 168 HK-derived segments while DR genomes contained up to ~40 segments originating from 168 ME (FIG. 2A). Recombination fragment sizes were distributed exponentially, ranging from <10 bp to >30 kbp with a typical total recombination of ~5% of the genome (FIG. 2B).

Figures 3A, 3B:
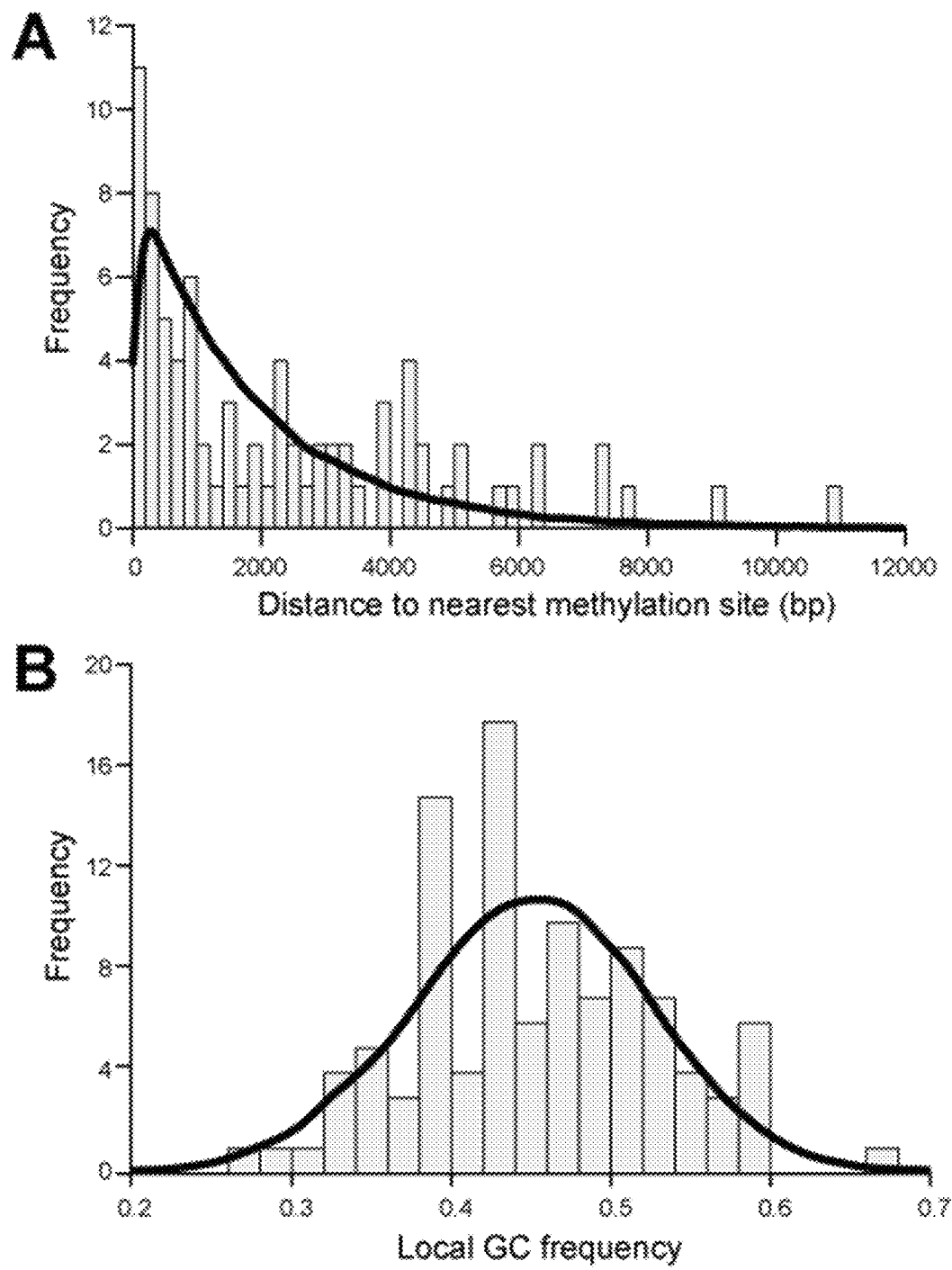
FIGS. 3A-3D. (A-C) Genome properties were calculated for the complete set 565 of recombination sites in 168 HK×3A27 ME prototrophic progeny (grey histograms) and equivalent randomly permuted recombination sites (black lines). Features analyzed are (A) distance between the boundary of a recombination site and the nearest methylation site, (B) GC frequency in a 256 bp window spanning the recombination boundary, and (C) SNP frequency in the same 256 bp window. Differences between actual and permuted distributions were not significant. (D) Population-level recombination was analyzed across the genome using a Continuous Wavelet Transformation analysis with Ricker Wavelets. The wavelet coefficient is plotted for each combination of genomic position and length scale. High wavelet coefficients indicate deviations from the baseline at a particular combination of position and length scale. Genomic positions of the selection markers are indicated; this population selected for recombination at the hisB marker and against recombination at the metE marker. Only the recombination hotspot at hisB is evident.
Figure 3C:
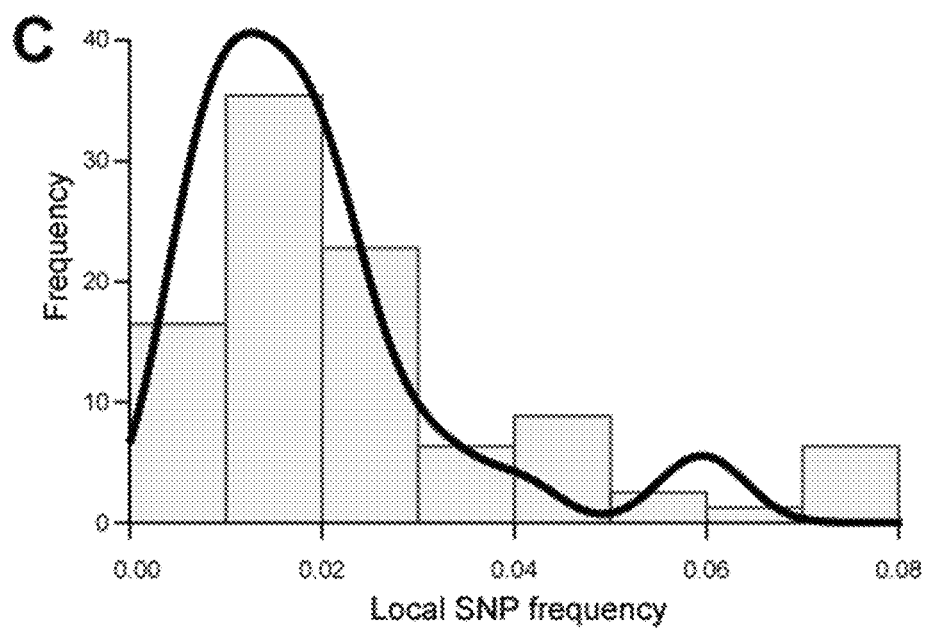
Figure 3D:
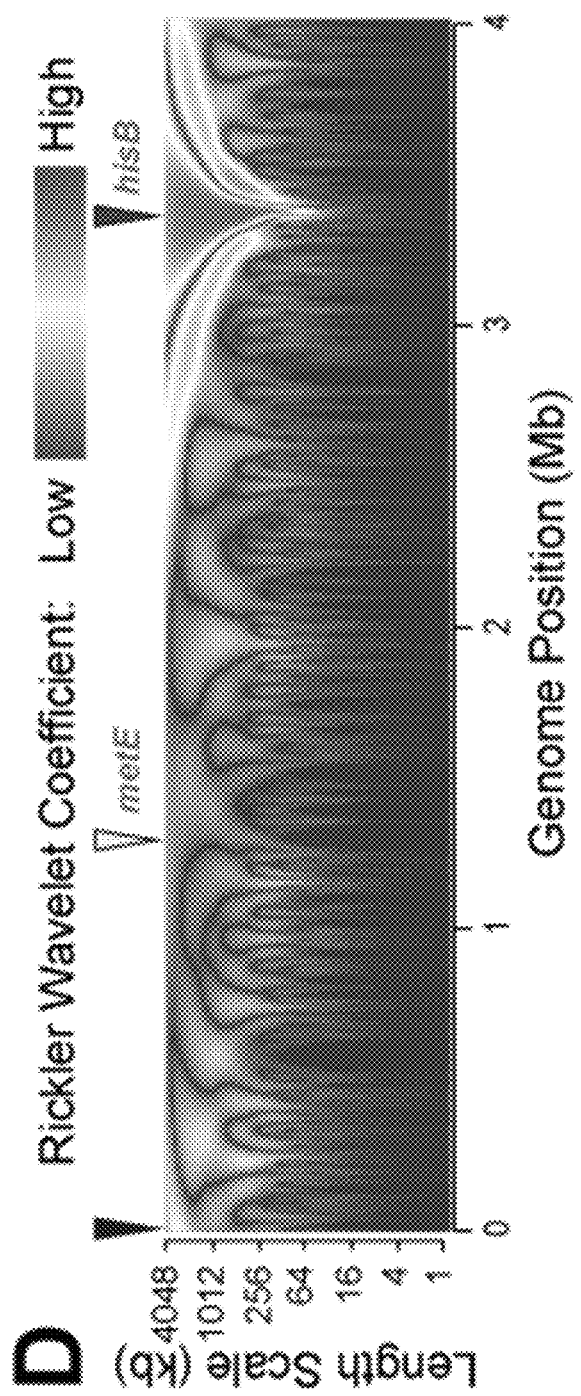

A variety of genomic features were analyzed to test their influence on recombination patterns. Recombination was not affected by local methylation patterns (FIG. 3A), local GC percentage (FIG. 3B), or local SNP density (FIG. 3C), suggesting that recombination is nearly random and therefore highly effective at breaking genetic linkages. Methylation loci were annotated from across the genome and were used to calculate distance to the nearest random position in the genome in permutation. Insertion sites (both 5' and 3' ends relative to the reference genome) were also measured for mean distance to random sites in permutation. Distance between methylation to random and insertion site to random had near identical overlap, indicating methylation loci do not have a significant effect on insertion patterns. Percent GC content and Percent Variants was calculated within windows up to 512 bp. More specifically, the middle position of the 512 bp window is the 5' or 3' end of both randomly placed in-silico generated insertions and actual insertion positions, e.g. the inventors scanned out from insertion ends 256 bp in both directions. Random insertions were modelled after existing insertion sizes with a minimum length of 512 bp so 5' and 3' ends don't overlap causing double counting of features. Percent variants were scanned both in the 5' and 3' direction from the ends of insertion sites and little to no bias was detected in the variant density of insertion sites to random insertion positions base pair windows. Thus, where recombination occurs it is highly detectable given the percent identity of this parent set. However, small insertions are likely to be missed in conserved areas since insertions were found form single variants inherited from the recessive parent.

Parent 3A27 has two methylation sites, with (reverse-complement) motifs GAYGNNNNNNCTT (SEQ ID NO: 1) and AAGNNNNNNCRTC (SEQ ID NO: 2) which were annotated using IGV 2.3.5. The percent of GC content was also examined at +/−256 bp windows (512 bp total) at known insertion sites compared to random 5' and 3' ends of in-silico generated insertions, again, GC content, like other features, did not have a differential distribution compared to random positions. To determine if some loci were more likely to recombine locally than other locations, the inventors summed all recessive parent markers from all individuals to a single vector and scanned it with a Continuous Wavelet Transformation. The most significant hot-spot for recessive parent markers was near the ≈3.3 Mbp position where the recessive parent selection marker was inherited. Wavelet transformation can find both high and low signal points and the region near the dominant parent selection marker shows no cold-spots for recombination, thus the inventors further conclude that recombination is not biased across the population by genomic features, nor any specific genomic location, with the exception of the recessive parent selection marker.

Figure 4A:
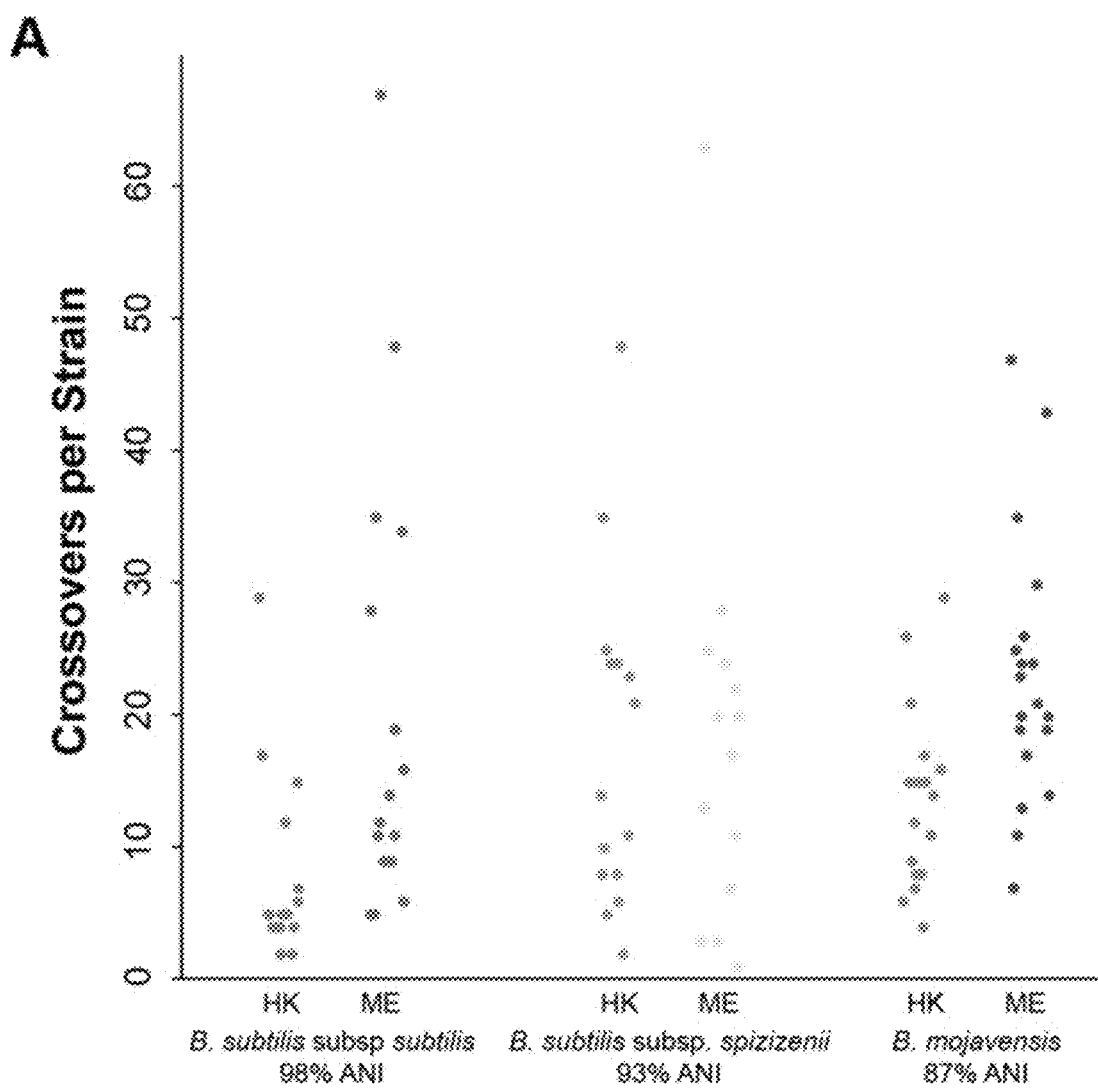
FIGS. 4A-4B. Genetic distance does not affect recombination. A double-resistant mutant of 3A27 was crossed with prototrophic strains of varying genetic distance. No significant differences were observed in (A) the number of recombination events per strain or (B) the distribution of recombination event size.
Figure 4B:
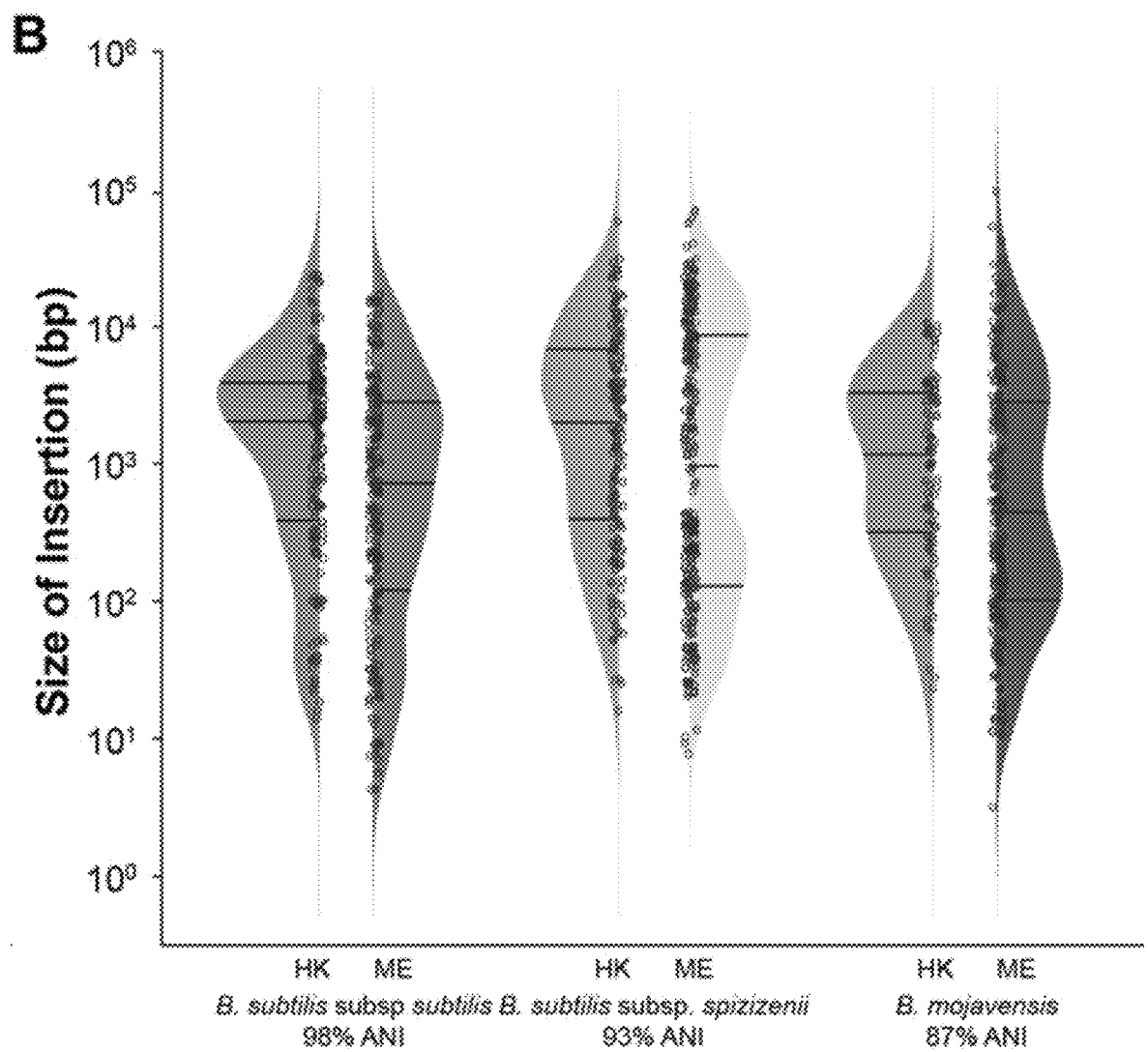

Strains 168 and RO-NN-1 are in the same subspecies and have approximately 98% average nucleotide identity (ANI) in shared genes. To better understand the role of nucleotide identity on recombination parameters, the inventors successfully shuffled RO-NN-1 ΔhisB::kan ΔmetE::erm with wild-type strains *B. subtilis* subsp. *subtilis* NCIB3610 (98% ANI), *B. subtilis* subsp. *spizizenii* TU-B-10 (93% ANI) and *B. mojavensis* RO-H-1 (87% ANI). The inventors were unable to generate recombinants using *B. amyloliquefaciens* FZB42 (78% ANI). In each successful example, they isolated and sequenced the genomes of approximately 16 strains from both potential recombinant genotypes, either ΔhisB::kan metE+ or ΔmetE::erm hisB+. The inventors observed no significant changes in the number of recombination events per strain (FIG. 4A) or the size distribution of those recombined segments (FIG. 4B).

The quantity of variants per shuffled population was relative to the percent identity shared between parents. The average indel (as a variant call site) had a mean size approximately 3-4 base pairs, and thus hypothetically did not augment genome size fluctuation, though true genome size is unknown from the short reads used in this study. Indels as markers yielded additional support to call crossover events. Both 3A27×2A11 populations appear to have higher insertion calls compared to other strains, likely due to their genetic divergence.

The methods utilize bacterial DNA recombination in *Bacillus subtilis* by crossing it to four different strains of varying percent identity. LD pruning methods are used to detect recombined genomic regions of *B. subtilis* shuffled populations. It is observed that strains with further divergence recombine less than more closely related strains. For instance, strains with 87% identity had less shuffled genomes than strains with 95% identity. The inventors developed three possible modified linear mixed model equations for association mapping of traits that account for population structure along a circular chromosome such as in bacterial species. The inventors demonstrated that recombination (shuffling) can be induced between bacterial species, that recombination can be quantified, and that association mapping can bridge phenotypic traits to loci within the genome.

In some embodiments, each parental strain has one of two antibiotic resistant genes and F1 offspring that survive both selection media would require having both loci, thus would have some level of recombination. Measuring this recombination required DNA sequencing of the genomes from F1 strains. Strain reads were aligned against the 3A27 RO-NN-1 reference (NCBI) genome using an in-house developed pipeline to call variants for SNPs and Indels. Paired end fastq files were first aligned against respective *B. subtilis* reference genomes using the BWA-MEM alignment tool to generate .sam files. Before samtools was used to convert to bam format, sam files were examined for reads that are non-uniquely mapping (mapping to more than one locus) and were removed from analysis via AWK regular expression to remove reads with low mapping quality. Post samtools conversion to bam, bam files were sorted and re-aligned to validate variants using common methods in picard tools and genomic analysis tool kit (GATK) from the Broad Institute. Once .bam files are refined they are converted to variant call format (.vcf) for individual samples through the GATK HaplotypeCaller function, then markers are validated using the same software's ValidateVariant function. VCF files are then compressed using bgzip and tabix and BCFTools was used to merge multiple VCFs across samples using the GNU parallel software.

Plink can filter, convert, and scan files for patterns of markers along a genome. The plink—indep-pairwise function can find regions of recombination at specific thresholds, flag said regions, and leave annotated marks as representative flags for recombinant loci. In this study, the inventors used PLINK2 to move a sliding window of 50 variants (SNPs or indels) at a time for variants with linkage disequilibrium using an R2 metric (—r2) with a threshold of 0.2 to set a representative variant flag. Scanning along the genome in this manner revealed various amounts of recombination in different strain by strain shuffles. The number of bases between flags reveals the hot and cold recombination regions in a genome. Strain shuffles 168E1×3A27K3 returned 6174 recombination hotspot flags. The shuffle 3A27E1K3×3A1 had 112 recombinant hotspots. The individuals derived from 168K3×3A27E1 had 5,239 flagged hotspots. The 3A27E1K3×28A5 shuffles returned 3,598 hotspot flags. A total of 512 hotspot flags were returned for the 3A27E1K3×2A11 shuffle. 3A27 and 3A1 are known to share high percent identity to one another. Due to the overlap of shared markers, recombination events could be frequent, yet not detectable. Strains 168 and 28A5 share fewer makers than 3A1, thus recombination is likely to be more detectable since the number of varying markers per 100 bases works well with modern read aligners like BWA-MEM. Though more relaxed read alignment could flag more loci the chances of reads mapping to many loci increase. Strain 2A11 had a substantial drop off of reads, likely due to the number of miss-matches allowed via BWA. These few problems can be remedied through larger sample sizes, multiple generations of already shuffled parents, and sweeping through a range of settings in each of a series of informatic software to call variants that will eventually be used for association studies.

Strains 168, 3A1, 2A11, and 2A85 were crossed against the 3A27 reference strain, thus markers were called in order to get metrics of bases between recombination events, variant density, and trait association mapping. QTL analysis examines patterns of overlapping variance between two data types, namely genomic markers and phenotypes, from a population of individuals. The inventors used GEMMA (Genome-wide Efficient Mixed Model Association) to detect associations between phenotypes and detected genomic variants. Rare variant testing is also of interest since rare alleles often have large contributions to phenotypes, but often require large sample sizes and high sequencing depth to reliably call rare variants. Recombinant areas are defined as regions of the genome that have variant calls derived from the interbreeding non-reference parent that have measurable linkage disequilibrium decay. All strains from every shuffle set were independently aligned as above for variants against the 3A27 genome to call variants. Using a population of 212 individuals, flagged variants were used to create synthetic phenotype data that was used to attempt recapturing the loci it was derived from using GEMMA. Recombination was frequent across strains, but often the percent identity of individuals to each parental strain was about 95% dominant one parent leaving few markers as valid test loci. With approximately 95% of the genome coming from one parent, a minor allele frequency of 0.05 or lower would be needed to re-capture synthetic loci and thus would require a study population of approximately 1,000 individuals. Two different paths forward will ensure success in QTL mapping in bacterial systems, one is to increase the amount of shuffled material, the inventors have demonstrated that some strains less randomly shuffle their DNA, while others have clear hot and cold spots, thus balanced marker shuffling across generations will ensure higher allele frequencies.

Example 3: Backcrossing

Strains 3A38 HK (*B. subtilis* subsp. *subtilis* NCIB3610 comI(Q12L) hisB::kan) and 3A27 ME (*B. subtilis* subsp. *subtilis* RO-NN-1 metE::ery) were shuffled as described in Example 1. Recombinant progeny were isolated based on their phenotypes (either wild-type or his$^-$ kan$^R$ met$^-$ ery$^R$) and resequenced. Individual genomes of recombinant strains were found to contain a majority of genetic markers from the 3A27 ME genome with randomly recombined segments of DNA from 3A38 HK that, on average, totaled approximately 5% of each genome. To further increase the fraction of genetic contributions from 3A38, the wild-type progeny pool from the first round of shuffling was shuffled with a double mutant strain of 3A38 (comI(Q12L) hisB::kan metE::ery), and the double-mutant progeny pool was shuffled with a wild-type strain of 3A38 (comI(Q12L)). Recombinant second generation progeny were selected, isolated, and resequenced. The genomes of these recombinant strains still contained a majority of genetic markers from parental strain 3A27 but, on average, had an increased fraction of recombined segments of DNA from parental strain 3A38.

Example 4: Diversification

Strains 3A27 DR (*B. subtilis* subsp. *subtilis* RO-NN-1 hisB::kan metE::ery) and 2A11 WT (*B. subtilis* subsp. *spizizenii* TU-B-10) were shuffled as described in Example 1. Recombinant progeny were isolated based on their phenotypes (either his$^-$ kan$^R$ or net ery$^R$) and resequenced. The genomes of recombinant strains were found to contain a majority of genetic markers from the 3A27 DR genome with randomly recombined segments of DNA from 2A11 WT. To introduce additional genetic variation, the ME progeny pool from the first round of shuffling was shuffled with a new parental strain, 168 HK (*B. subtilis* subsp. *subtilis* 168 hisB::kan). Recombinant second generation progeny were selected, isolated, and resequenced. Individual genomes of these recombinant strains contained genetic markers from all three parental strains: 3A27, 2A11, and 168.

Example 5: Tracking Parental Contributions to Recombinant Progeny

Figure 8A:
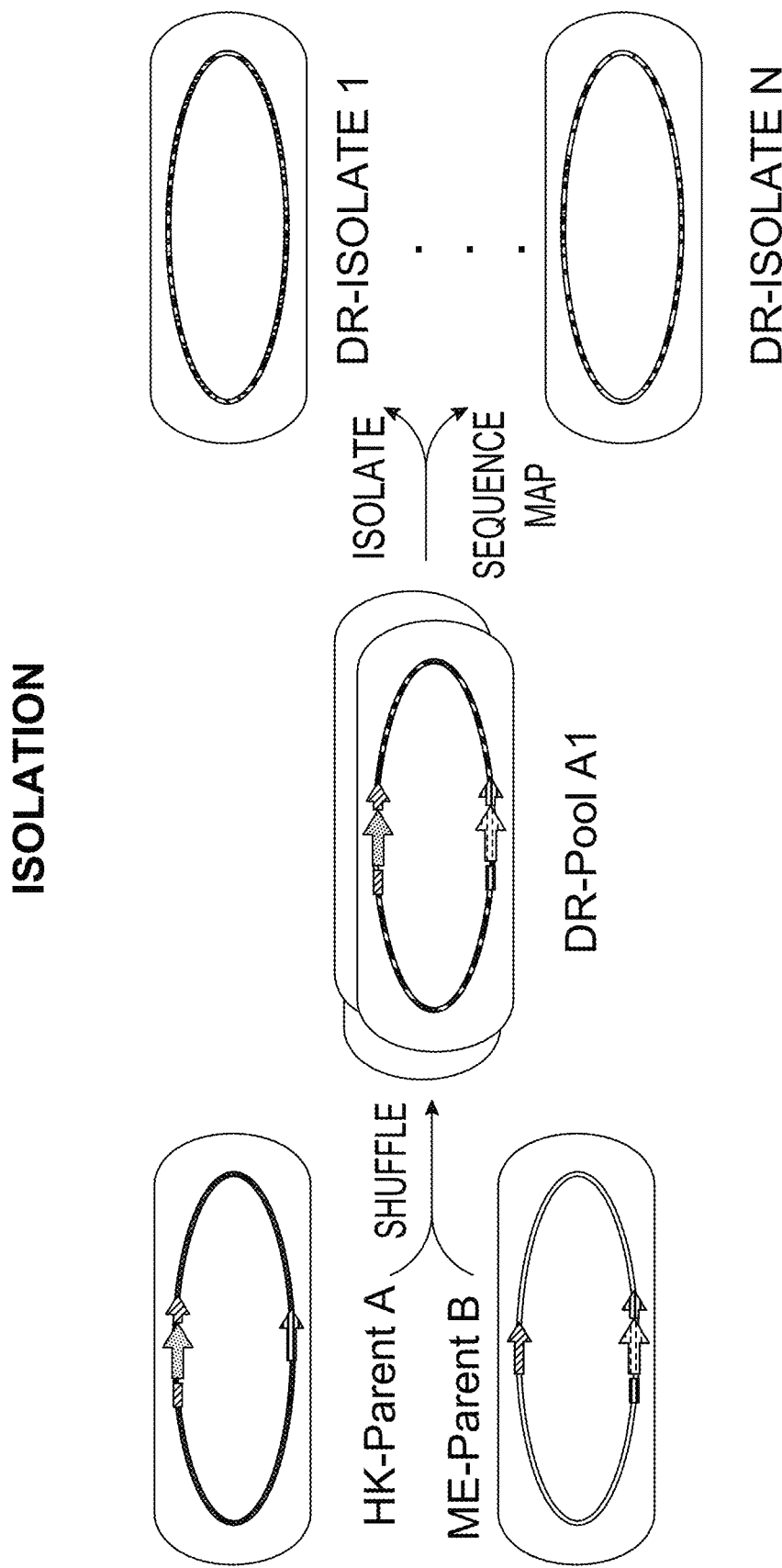
FIG. 8A-8B. Exemplary types of sequencing. (A) Isolation sequencing. (B) Pooled sequencing.
Figure 8B:
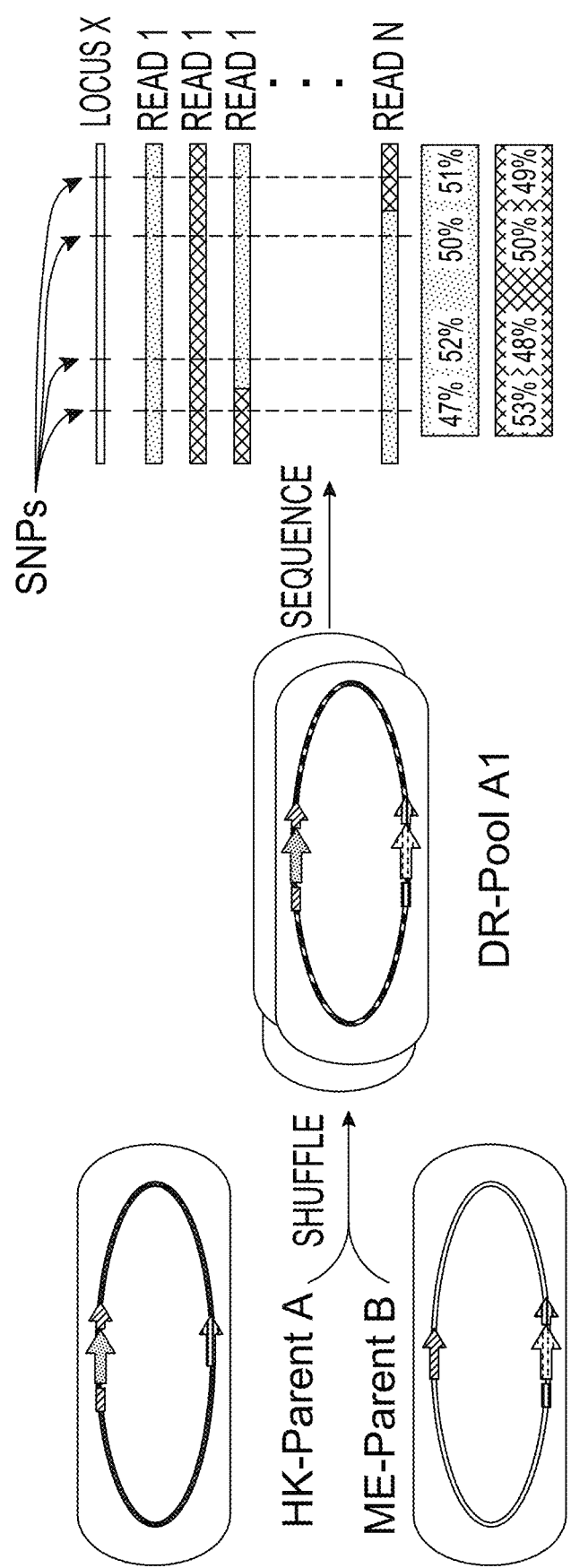

Two methods were used to identify differential genetic contributions from parents to progeny. In the first method (FIG. 8A), individual recombinant strains were isolated after shuffling. The recombinant progeny were resequenced and the genomes were mapped to each of the parents. Throughput is limited (typically 10-20 strains resequenced per shuffle, with a limited number of recombination events per strain), but the genetic contribution from each parent could be estimated. In this method, heterogeneity of recombination can be assessed (e.g. whether all strains have, say, 20% genetic contributions from the minor parent or whether some strains have 40% and some have 0%). In the second method (FIG. 8B), mixed progeny pools are sequenced together. Individual reads are aligned to the parental genomes, and reads at each variable locus can be mapped to the different parents to quantitatively measure their fractional genetic contributions. This method measures genetic contributions from each parent at each locus independently. Deep sequencing provides accurate measurements, but phasing is lost; a pool in which half of the population is identical to parent A and half is identical to parent B is difficult to distinguish from a pool in which all of the population is evenly genetically mixed.

Example 6: Genetic Mapping of the Ability to Grow Under Restrictive Conditions

Strains 168 HK (*B. subtilis* subsp. *subtilis* trpC2 hisB::kan) and 3A27 ME (*B. subtilis* subsp. *subtilis* RO-NN-1 metE::ery) were shuffled as described in Example 1. Recombinant progeny were isolated on Spizizen minimal medium containing 400 µM tryptophan. These progeny were resequenced and variable genetic markers from each parent were determined. The progeny were also phenotyped for their ability to grow in Spizizen minimal medium without tryptophan. The parental strain 168 HK cannot grow under these conditions due to a 3 bp deletion in the trpC gene, while the 3A27 ME parent can. Out of 24 recombinant isolates tested, 2 isolates were unable to grow in the absence of exogenous tryptophan. Comparing the genomes of the recombinant isolates, only one genetic locus was present in both trp$^-$ isolates and absent from all of the 24 trp$^+$ isolates. This locus comprised 29 bp internal to the trpC gene that contains four genetic variants including the causal 3 bp deletion. Based solely on measured genotypes and phenotypes of shuffled bacteria, the phenotype could be correctly mapped with sub-gene resolution.

Example 7: Genetic Mapping of Production of a Target Biochemical

Strains 168 HK (*B. subtilis* subsp. *subtilis* trpC2 hisB::kan) and 3A27 ME (*B. subtilis* subsp. *subtilis* RO-NN-1 metE::ery) were shuffled as described in Example 1. Recombinant progeny were isolated on Spizizen minimal medium containing 400 µM tryptophan. Some subsets of recombinant strains were observed to change colors from beige to red during prolonged incubation on Spizizen minimal agar containing 400 µM tryptophan. Out of 24 recombinant isolates tested, 5 isolates acquired this pigmented phenotype. Comparing the genomes of the recombinant isolates, only one genetic locus was present in all 5 of the pigmented strains and absent in the remaining 19 unpigmented strains. This locus comprised a gene cluster, totaling approximately 5 kb and expressing 5 genes, that was present in the 168 HK parent and absent in the 3A27 ME parent. The 5 pigmented strains acquired this gene cluster through recombination. The gene cluster encodes enzymes involved in biosynthesis of the siderophore pulcherrimin, which has a characteristic red color when bound to iron. Pulcherrimin synthesis in the pigmented strains was then confirmed using liquid chromatography-mass spectrometry. Based solely on measured genotypes and phenotypes of shuffled bacteria, the phenotype could be correctly mapped to the causal gene cluster.

inducing at least two rounds of genomic recombination, wherein the at least two rounds of genomic recombination comprises
(i) inducing a first round of genomic recombination between a population of a first starting strain and a population of a second starting strain to obtain first generation progeny bacteria,
(ii) selecting among the first generation progeny bacteria to obtain two populations of bacteria that have undergone genomic recombination using two different selective media, wherein each selective medium kills both starting bacterial strains and allows only one of the two populations of the first generation progeny bacteria to live,
(iii) inducing a second round of genomic recombination between one of the two selected populations of the first generation progeny bacteria and a population of bacteria that comprises a selectable marker compatible with the first selected population of the first generation progeny bacteria and that is selected from the group consisting of:

What is claimed is:

1. A method for identifying quantitative trait-loci in bacteria comprising:
   providing two starting bacterial strains, wherein the two starting strains comprise selectable markers compatible with each other in that either at least one of the two starting bacterial strains is a wild type prototroph strain without an antibiotic resistance gene and the other starting bacterial strain is double auxotroph and comprises two different antibiotic resistance genes, or the two starting bacterial strains are each a single auxotroph strain comprising an antibiotic resistance gene and differ from each other in auxotrophy and antibiotic resistance;

(a) the other of the two selected populations of the first generation progeny bacteria,
   (b) a population of a strain that is otherwise genetically identical to one of the two starting strains,
   (c) a population of a strain that is different from both starting strains, and
   (d) a population of bacteria selected from progeny bacteria from induced genomic recombination between two different starting strains, thereby obtaining second generation progeny bacteria;
   (iv) selecting among the second generation progeny bacteria for two populations of bacteria that have undergone genomic recombination using two selective media, wherein each selective medium kills both populations of bacteria used in the second round of genomic recombination, and allows only one of the two populations of the second generation progeny bacteria to live, and (v) obtaining the selected two populations of the second generation progeny bacteria as two populations of a final generation progeny bacteria, or inducing at least one more round of genomic recombination and selecting between a first selected population of the second generation progeny bacteria and a population of bacteria that comprises a selectable marker compatible with the first selected population of the second generation progeny bacteria to obtain two populations of a final generation progeny bacteria;

determining the sequences of the genomes of the two populations of the final generation progeny bacteria, thereby determining genetic variations within the genomes of the two populations the final generation progeny bacteria;

determining at least one phenotype of the two populations of the final generation progeny bacteria; and performing a population-wide analysis to identify genetic variations that associate with the at least one phenotype, thereby identifying quantitative-trait loci that are associated with the at least one phenotype.

2. The method of claim 1, wherein the antibiotic resistance genes are inserted into the bacterial genomes to disrupt genes essential for bacterial survival.

3. The method of claim 1, wherein the at least one phenotype comprises one or more of bacterial growth rate, resistance to a chemical compound, production of a target biochemical, ability to transfer into new environmental niche, ability to persist in a new environmental niche, ability to modulate a host phenotype when established in the host microbiome, ability to inhibit growth of a target organism, and ability to grow under restrictive conditions.

4. The method of claim 1, wherein the genomic recombination at each round is achieved by protoplast fusion-induced homologous recombination.

5. The method of claim 1, wherein the bacteria are Gram-negative.

6. The method of claim 5, wherein the Gram-negative bacteria are selected from the group consisting of *Pseudomonas, Novosphingobium, Sphingobium, Sphingomonas, Escherichia, Zymomonas,* and *Cupriavidus.*

7. The method of claim 5, wherein the genomic recombination at each round is achieved by protoplast fusion-induced homologous recombination comprising (a) treating the bacterial strains with an antibiotic that inhibits peptidoglycan biosynthesis; and (b) inducing the treated bacterial strains to undergo protoplast fusion in a high osmolarity medium comprising between 0.5 M and 1.2 M sucrose.

8. The method of claim 7, wherein the antibiotic that inhibits peptidoglycan biosynthesis is Fosfomycin.

9. The method of claim 7, wherein the protoplast fusion is achieved by chemofusion or electrofusion.

10. The method of claim 9, wherein the chemofusion is achieved using polyethylene glycol.

11. The method of claim 1, wherein the bacteria are Gram-positive.

12. The method of claim 11, wherein the Gram-positive bacteria are selected from the group consisting of genera *Bacillus, Corynebacterium, Streptomyces, Propionibacterium, Clostridium,* and *Lactobacillus.*

13. The method of claim 11, wherein the genomic recombination at each round is achieved by protoplast fusion-induced homologous recombination comprising (a) treating the bacterial strains with lysozyme, and (b) inducing the treated bacterial strains to undergo protoplast fusion in a high osmolarity medium comprising between 0.5 M and 1.2 M sucrose.

14. The method of claim 13, wherein the protoplast fusion is achieved by chemofusion or electrofusion.

15. The method of claim 14, wherein the chemofusion is achieved using polyethylene glycol.

16. The method of claim 1, wherein the population-wide analysis comprises:

(a) mapping the sequences of each strain of the final generation progeny bacteria to the starting bacterial strains; and (b) determining the presence of single nucleotide polymorphisms and insertions based on the mapping in (a).

17. The method of claim 16, wherein the method further comprises:

(c) performing de novo assembly of genomes of each strain of the final generation progeny bacteria; and (d) determining structural variants by comparing the assembled genomes of the final generation progeny bacteria to the genomes of the starting bacterial strains.

18. The method of claim 1, wherein the population-wide analysis comprises a variant calling step that comprise mapping the genotypes of the final generation progeny bacterial strains to the genotype of the starting bacterial strains.

19. The method of claim 1, wherein the population-wide analysis comprises a pruning step to cluster away variants that have indistinguishable association to a given phenotype via a parameter sweep function that scans every variant as a potential start position for pruning.

20. The method of claim 1, wherein the population-wide analysis comprises a haplotype calling step.

21. The method of claim 1, wherein the population-wide analysis comprises performing a Continuous Wavelet Transform Analysis.

* * * * *

```
                         SEQUENCE LISTING

<160> NUMBER OF SEQ ID NOS: 2

<210> SEQ ID NO 1
<211> LENGTH: 13
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (5)..(10)
<223> OTHER INFORMATION: n is a, c, g, t or u

<400> SEQUENCE: 1
gaygnnnnnn ctt                                                          13

<210> SEQ ID NO 2
<211> LENGTH: 13
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (4)..(9)
<223> OTHER INFORMATION: n is a, c, g, t or u

<400> SEQUENCE: 2
aagnnnnnnc rtc                                                          13
```